(12) United States Patent
Horner et al.

(10) Patent No.: US 10,758,856 B2
(45) Date of Patent: Sep. 1, 2020

(54) FILTER MEDIUM COMPRESSION SYSTEM FOR SMOKE EVACUATION

(71) Applicant: Megadyne Medical Products, Inc., Draper, UT (US)

(72) Inventors: Shawn K. Horner, Woods Cross, UT (US); Jason Harris, Lebanon, OH (US); Frederick Shelton, Hillsboro, OH (US); David Yates, West Chester, OH (US)

(73) Assignee: Megadyne Medical Products, Inc., Draper, UT (US)

( * ) Notice: Subject to any disclaimer, the term of this patent is extended or adjusted under 35 U.S.C. 154(b) by 95 days.

(21) Appl. No.: 15/826,342

(22) Filed: Nov. 29, 2017

(65) Prior Publication Data

US 2019/0160410 A1    May 30, 2019

(51) Int. Cl.
*B01D 53/04* (2006.01)
*A61B 18/00* (2006.01)
(Continued)

(52) U.S. Cl.
CPC .......... *B01D 46/0036* (2013.01); *A61B 18/00* (2013.01); *A61B 18/14* (2013.01);
(Continued)

(58) Field of Classification Search
CPC ................ B01D 46/0036; B01D 53/04; B01D 46/0023; A61B 18/00; A61B 18/14;
(Continued)

(56) References Cited

U.S. PATENT DOCUMENTS

| 1,165,288 A | 12/1915 | Rimmer |
| 1,789,194 A | 1/1931 | Rockwell |

(Continued)

FOREIGN PATENT DOCUMENTS

| WO | 9408698 | 4/1994 |
| WO | 2016142690 | 9/2016 |

(Continued)

OTHER PUBLICATIONS

Non-Final Office Action for U.S. Appl. No. 29/627,793 dated Oct. 29, 2018.
(Continued)

*Primary Examiner* — Minh Chau T Pham
(74) *Attorney, Agent, or Firm* — Workman Nydegger

(57) ABSTRACT

A filter includes (i) a filter body, (ii) a front cap associated with a first end of the filter body and coupled to and receiving smoke from a vacuum hose, (iii) a back cap associated with a second end of the filter body and having a filter exhaust sized and shaped to associate with and communicate suction from a smoke evacuation system, (iv) a compressed carbon reservoir disposed within the filter body between the front cap and the back cap, and (v) a flexible porous barrier disposed on at least a first side of the compressed carbon reservoir. The compressed carbon reservoir is under a compressive bias by the flexible porous barrier that transitions from a flexed state to a partially relaxed state in response to the compressed carbon reservoir reducing in volume.

20 Claims, 16 Drawing Sheets

(51) Int. Cl.
  *A61B 18/14* (2006.01)
  *B01D 46/00* (2006.01)
  *A61B 18/12* (2006.01)
(52) U.S. Cl.
  CPC ......... *B01D 46/0023* (2013.01); *B01D 53/04* (2013.01); *A61B 18/1206* (2013.01); *A61B 18/1402* (2013.01); *A61B 2018/00595* (2013.01); *A61B 2018/00601* (2013.01); *A61B 2218/008* (2013.01); *A61M 2205/75* (2013.01)
(58) Field of Classification Search
  CPC .......... A61B 18/1402; A61B 2218/008; A61B 2018/00595; A61B 2018/00601; A61B 18/1206; A61M 2205/75
  USPC .............. 55/385.1, 420, 482, 467, 486, 503; 95/273, 286; 604/35, 319, 322, 902; 454/187
  See application file for complete search history.

(56) References Cited

U.S. PATENT DOCUMENTS

| | | |
|---|---|---|
| 2,577,606 A | 12/1951 | Conley |
| 3,815,752 A | 6/1974 | Hoffman et al. |
| 3,841,490 A | 10/1974 | Hoffman et al. |
| 4,116,649 A * | 9/1978 | Cullen .................. B01D 15/00 206/204 |
| 4,157,234 A | 6/1979 | Shaffer et al. |
| 4,396,206 A | 8/1983 | Tsuge et al. |
| 4,619,672 A | 10/1986 | Robertson |
| 4,701,193 A | 10/1987 | Robertson et al. |
| 4,788,298 A | 11/1988 | Billet et al. |
| 4,810,269 A | 3/1989 | Stackhouse et al. |
| 4,826,513 A | 5/1989 | Stackhouse et al. |
| 4,988,839 A | 1/1991 | Wertz et al. |
| 5,108,389 A | 4/1992 | Comescu |
| 5,144,178 A | 9/1992 | Popper |
| 5,160,334 A | 11/1992 | Billings et al. |
| 5,221,192 A | 6/1993 | Heflin et al. |
| 5,228,939 A | 7/1993 | Nicolas et al. |
| 5,242,474 A | 9/1993 | Herbst et al. |
| 5,288,489 A | 2/1994 | Skalla et al. |
| 5,318,516 A | 6/1994 | Comescu |
| 5,336,218 A | 8/1994 | Linhares |
| 5,342,349 A | 8/1994 | Kaufman |
| D357,738 S | 4/1995 | Kaufman |
| 5,423,779 A | 6/1995 | Yeh |
| 5,431,650 A | 7/1995 | Comescu |
| 5,507,859 A * | 4/1996 | Kaiser ................. B01D 46/0091 55/373 |
| 5,522,808 A | 6/1996 | Skalla |
| 5,597,385 A | 1/1997 | Moerke |
| 5,620,441 A | 4/1997 | Greff et al. |
| 5,674,219 A | 10/1997 | Monson et al. |
| 5,690,480 A | 11/1997 | Suzuki et al. |
| 5,853,410 A | 12/1998 | Greff et al. |
| 5,874,052 A | 2/1999 | Holland |
| 5,910,291 A | 6/1999 | Skalla et al. |
| 5,992,413 A | 11/1999 | Martin et al. |
| 6,050,792 A | 4/2000 | Shaffer |
| 6,110,259 A * | 8/2000 | Schultz ................. A61B 18/00 55/385.1 |
| 6,129,530 A | 10/2000 | Shaffer |
| 6,203,590 B1 | 3/2001 | Byrd |
| 6,203,762 B1 | 3/2001 | Skalla et al. |
| 6,331,246 B1 | 12/2001 | Beckham |
| 6,439,864 B1 | 8/2002 | Shaffer |
| 6,511,308 B2 | 1/2003 | Shaffer |
| 6,524,307 B1 | 2/2003 | Palmerton et al. |
| 6,544,210 B1 | 4/2003 | Trudel et al. |
| 6,585,791 B1 | 7/2003 | Garito et al. |
| 6,589,318 B2 | 7/2003 | Schultz et al. |
| 6,592,543 B1 | 7/2003 | Wortrich et al. |
| 6,616,722 B1 | 9/2003 | Cartellone |
| 6,663,698 B2 | 12/2003 | Mishin et al. |
| D485,339 S | 1/2004 | Klug |
| 6,709,248 B2 | 3/2004 | Fujioka et al. |
| 6,736,620 B2 | 5/2004 | Satoh |
| 6,758,885 B2 | 7/2004 | Leffel et al. |
| 6,786,707 B2 | 9/2004 | Kim |
| D513,314 S | 12/2005 | Iddings |
| 7,014,434 B2 | 3/2006 | Fujioka et al. |
| D521,137 S | 5/2006 | Khalil |
| D545,955 S | 7/2007 | Arlas |
| 7,258,712 B2 | 8/2007 | Schultz et al. |
| D553,228 S | 10/2007 | Virr |
| 7,276,052 B2 | 10/2007 | Kobayashi et al. |
| D555,803 S | 11/2007 | Galrto |
| 7,294,116 B1 | 11/2007 | Ellman et al. |
| D574,323 S | 8/2008 | Waaler |
| 7,465,156 B2 | 12/2008 | Lee |
| 7,497,340 B2 | 3/2009 | Hershberger et al. |
| 7,597,731 B2 | 10/2009 | Palmerton |
| D616,986 S | 6/2010 | Biegen |
| D625,399 S | 10/2010 | Horiguchi |
| D626,204 S | 10/2010 | Morgan |
| 7,819,957 B2 | 10/2010 | Roberts et al. |
| 7,942,655 B2 | 5/2011 | Shaffer |
| 8,033,798 B2 | 10/2011 | Suh et al. |
| 8,142,175 B2 | 3/2012 | Duppert et al. |
| 8,147,577 B2 * | 4/2012 | Palmerton .............. A61B 18/00 55/385.1 |
| 8,190,398 B2 | 5/2012 | Kitaguchi et al. |
| D666,704 S | 9/2012 | Osendorf |
| 8,298,420 B2 | 10/2012 | Burrows |
| 8,556,570 B2 | 10/2013 | Ishihara |
| 8,608,816 B2 * | 12/2013 | Palmerton ........... A61M 1/0001 55/319 |
| 8,684,705 B2 | 4/2014 | Magoon et al. |
| 8,727,744 B2 | 5/2014 | Magoon et al. |
| 9,011,366 B2 | 4/2015 | Dean et al. |
| 9,028,230 B2 | 5/2015 | Shaffer |
| 9,067,030 B2 | 6/2015 | Stearns et al. |
| 9,074,598 B2 | 7/2015 | Shaffer et al. |
| D736,933 S | 8/2015 | Qiu |
| D737,449 S | 8/2015 | Zheng |
| 9,199,047 B2 | 12/2015 | Stearns et al. |
| 9,215,984 B2 | 12/2015 | Loske |
| 9,366,254 B2 | 6/2016 | Murakami |
| 9,387,295 B1 | 7/2016 | Mastri et al. |
| 9,387,296 B1 | 7/2016 | Mastri et al. |
| D764,649 S | 8/2016 | Ko |
| 9,415,160 B2 * | 8/2016 | Bonano ................. A61M 5/165 |
| 9,435,339 B2 | 9/2016 | Calhoun et al. |
| 9,474,512 B2 | 10/2016 | Blackhurst et al. |
| 9,532,843 B2 | 1/2017 | Palmerton |
| 9,549,849 B2 | 1/2017 | Charles |
| 9,579,428 B1 | 2/2017 | Reasoner et al. |
| D783,178 S | 4/2017 | Mead |
| D802,024 S | 11/2017 | Aoki |
| 9,867,914 B2 * | 1/2018 | Bonano ................. A61M 1/0001 |
| 9,943,355 B2 | 4/2018 | Babini |
| 2004/0223859 A1 | 11/2004 | Sharp |
| 2005/0000196 A1 | 1/2005 | Schultz |
| 2005/0189283 A1 | 9/2005 | Smit et al. |
| 2005/0263004 A1 | 12/2005 | Larsen et al. |
| 2006/0099096 A1 | 5/2006 | Shaffer et al. |
| 2007/0066970 A1 | 3/2007 | Ineson |
| 2009/0022613 A1 | 1/2009 | Dai et al. |
| 2011/0067699 A1 | 3/2011 | Caruso |
| 2011/0203585 A1 | 8/2011 | Cozean et al. |
| 2013/0231606 A1 | 9/2013 | Stearns et al. |
| 2014/0356207 A1 | 12/2014 | Yang |
| 2015/0224237 A1 | 8/2015 | Reasoner et al. |
| 2015/0273381 A1 | 10/2015 | Stoner et al. |
| 2016/0000494 A1 | 1/2016 | Comescu |
| 2016/0001102 A1 | 1/2016 | Huh |
| 2016/0287817 A1 | 10/2016 | Mastri et al. |
| 2016/0367266 A1 | 12/2016 | Palmerton et al. |
| 2017/0014557 A1 | 1/2017 | Minskoff et al. |
| 2017/0014560 A1 | 1/2017 | Minskoff et al. |
| 2017/0095603 A1 | 4/2017 | Cho |

(56) References Cited

U.S. PATENT DOCUMENTS

| | | | |
|---|---|---|---|
| 2017/0165725 | A1 | 6/2017 | Hersey et al. |
| 2017/0181788 | A1 | 6/2017 | Galley |
| 2019/0159830 | A1 | 5/2019 | Horner et al. |
| 2019/0160409 | A1 | 5/2019 | Horner et al. |

FOREIGN PATENT DOCUMENTS

| | | |
|---|---|---|
| WO | 201703712 | 1/2017 |
| WO | 2017/066720 | 4/2017 |
| WO | 2017112684 | 6/2017 |

OTHER PUBLICATIONS

International Search Report and Written Opinion for PCT/IB2018/059377 dated Mar. 6, 2019.
Non-Final Office Action for U.S. Appl. No. 15/826,344 dated Sep. 12, 2019.
Notice of Allowance for U.S. Appl. No. 15/826,344 dated Jan. 23, 2020.
Notice of Allowance for U.S. Appl. No. 15/826,344 dated Apr. 22, 2020.
Non-Final Office Action for U.S. Appl. No. 29/627,794 dated Jul. 10, 2019.
Non-Final Office Action for U.S. Appl. No. 29/627,794 dated Feb. 19, 2020.
International Search Report and Written Opinion for PCT/IB2018/059375 dated May 7, 2019.
Exam Report for MX/f/2018/001583 dated Jan. 20, 2020.
U.S. Appl. No. 29/627,794, dated Nov. 29, 2017.
Bovie 35 hour filter found online [Sep. 11, 2018] - http://www.boviemedical.com/smoke-shark-ii/.
"Megadyne Surgical Smoke Evacuation System found online [Sep. 11, 2018]-http://www.hcp-austria.com/Minivac%20Smoke%20Evacuators.html".
Non-Final Office Action for application No. 29/627,793 dated Oct. 29, 2018.

* cited by examiner

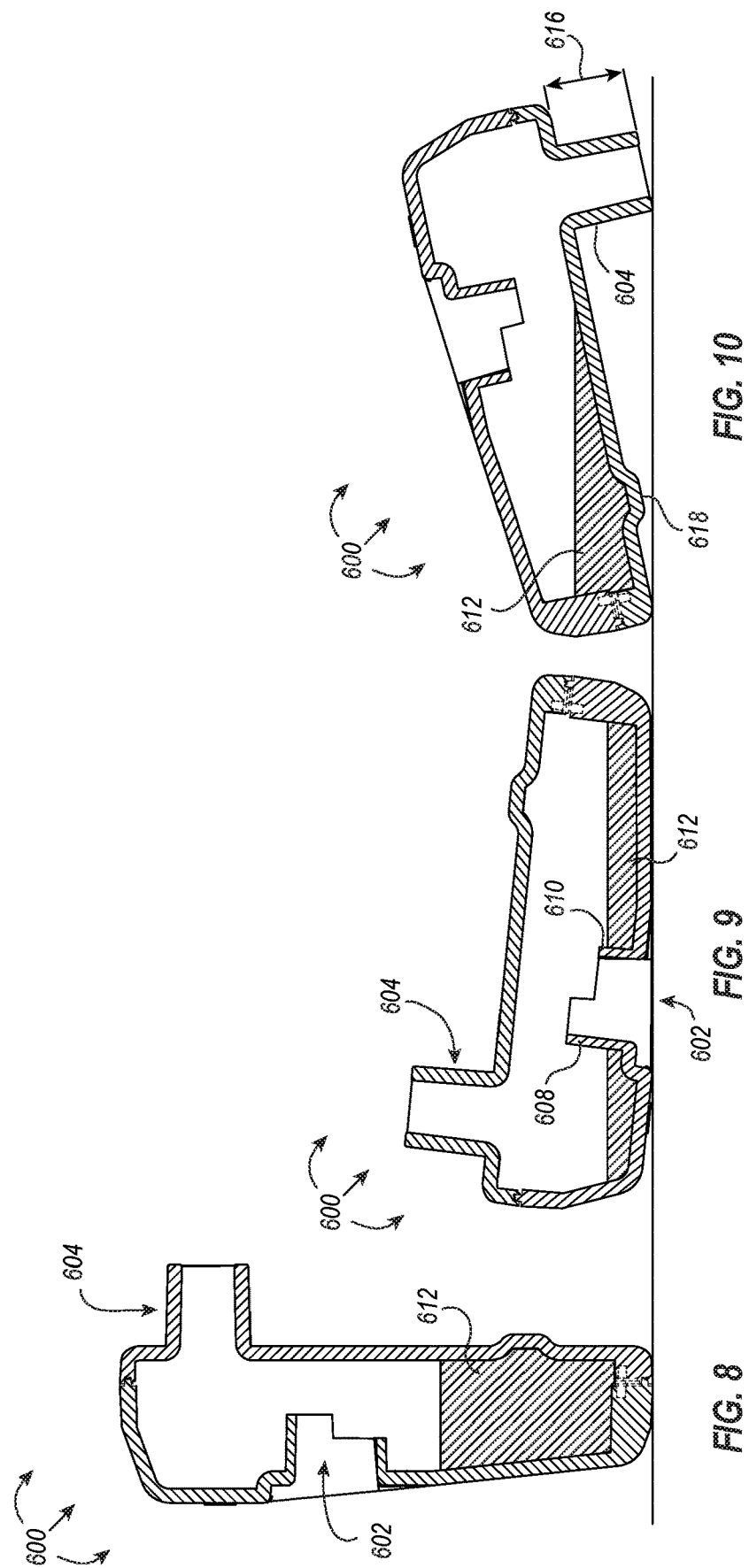

FILTER MEDIUM COMPRESSION SYSTEM FOR SMOKE EVACUATION

BACKGROUND

Technical Field

The present disclosure relates to smoke evacuation systems used in electrosurgical systems. More specifically, the present disclosure relates to apparatus and methods of controlling flow parameters of a smoke evacuation system.

The Relevant Technology

As is known to those skilled in the art, modern surgical techniques typically employ radio frequency (RF) power to cut tissue and coagulate bleeding encountered in performing surgical procedures. This type of surgery is known as electrosurgery. Electrosurgery is widely used and offers many advantages, including the use of a single surgical instrument for both cutting and coagulating tissue. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue through cauterization. The return electrode carries the same RF signal provided to the electrode or tip of the electrosurgical instrument, after it passes through the patient, thus providing a path back to the electrosurgical generator.

Electrosurgical instruments communicate electrical energy to a target tissue of a patient to cut the tissue and/or cauterize blood vessels within and/or near the target tissue. This cauterization results in smoke released into the air that can be unpleasant, obstructive of the view of a practitioner. Many electrosurgical systems may therefore employ an evacuation system that captures the resulting smoke and directs it through a filter and exhaust port, away from practitioners and/or patients. A smoke evacuation system typically creates suction directed at the smoke using fans to draw the smoke through a tube connecting the surgical instrument to an exhaust port.

Smoke evacuation systems often use filters in order to remove unwanted pollutants from the smoke exhaust before the air is released from the exhaust port. Periodically replacing filters is necessary for the smoke evacuation system to remain effective.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to smoke evacuation systems. More specifically, the present disclosure relates to a filter for a smoke evacuation device. Carbon reservoir based air filters can reduce in volume during use. This can negatively impact the efficiency of filters, and depending on the degree of volumetric collapse within the carbon reservoir, it can prevent the carbon reservoir from adequately filtering. The filters of the present disclosure maintain a compact, gapless carbon reservoir, or at least reduce the gaps formed within carbon reservoirs during use. Other features enable processing smoke in three stages to remove fluids, particulates, and chemical contaminants.

In an embodiment, a filter includes (i) a filter body, (ii) a front cap associated with a first end of the filter body and coupled to and receiving smoke from a vacuum hose, (iii) a back cap associated with a second end of the filter body and having a filter exhaust sized and shaped to associate with and communicate suction from a smoke evacuation system, (iv) a compressed carbon reservoir disposed within the filter body between the front cap and the back cap, and (v) a flexible porous barrier disposed on at least a first side of the compressed carbon reservoir.

In an embodiment, a replaceable filter for processing smoke derived from electrosurgery includes (i) a filter body, (ii) a front cap associated with a first end of the filter body, (iii) a back cap associated with a second end of the filter body and configured to receive suction, (iv) one or more particulate filters disposed within the filter body between the front cap and the back cap, (v) a compressed carbon reservoir disposed within the filter body between the one or more particulate filters and the back cap, and (vi) a flexible porous barrier disposed on at least a first side of the compressed carbon reservoir.

In an embodiment, a three-stage filter for processing smoke derived from electrosurgery includes a first stage for removing one or more fluids from the smoke, a second stage for removing particulates, and a third stage having a compressed carbon reservoir. The first stage can include a fluid trap having a fluid trap inlet port and a fluid trap exhaust port. The fluid trap inlet port extends into an interior chamber of the fluid trap and couples to and receives smoke from a vacuum hose. The fluid trap exhaust port is positioned opposite and above the fluid trap inlet port and defines an open channel between an interior chamber of the fluid trap, where one or more fluids extracted from the smoke are retained, and the second stage of the three-stage filter. In some embodiments, the second-stage removes particulates using one or more particulate filters, such as a coarse media filter and an ultra-low penetration air (ULPA) filter in series. In some embodiments, the third stage can be under a compressive bias by a flexible porous barrier. The flexible porous barrier can transition from a flexed state to a partially relaxed state in response to the compressed carbon reservoir reducing in volume, which in some embodiments is caused by settling of the compressed carbon reservoir or pressure from suction applied to the compressed carbon reservoir.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 8 illustrates a simplified vertical cross-section of the exemplary fluid trap depicted in FIG. 5 having fluid collected therein and in an upright position;

FIG. 9 illustrates a simplified vertical cross-section of the exemplary fluid trap depicted in FIG. 5 having fluid collected therein and positioned on a surface inlet-side down;

FIG. 10 illustrates a simplified vertical cross-section of the exemplary fluid trap depicted in FIG. 5 having fluid collected therein and positioned on a surface inlet side up;

DETAILED DESCRIPTION

Figure 1:
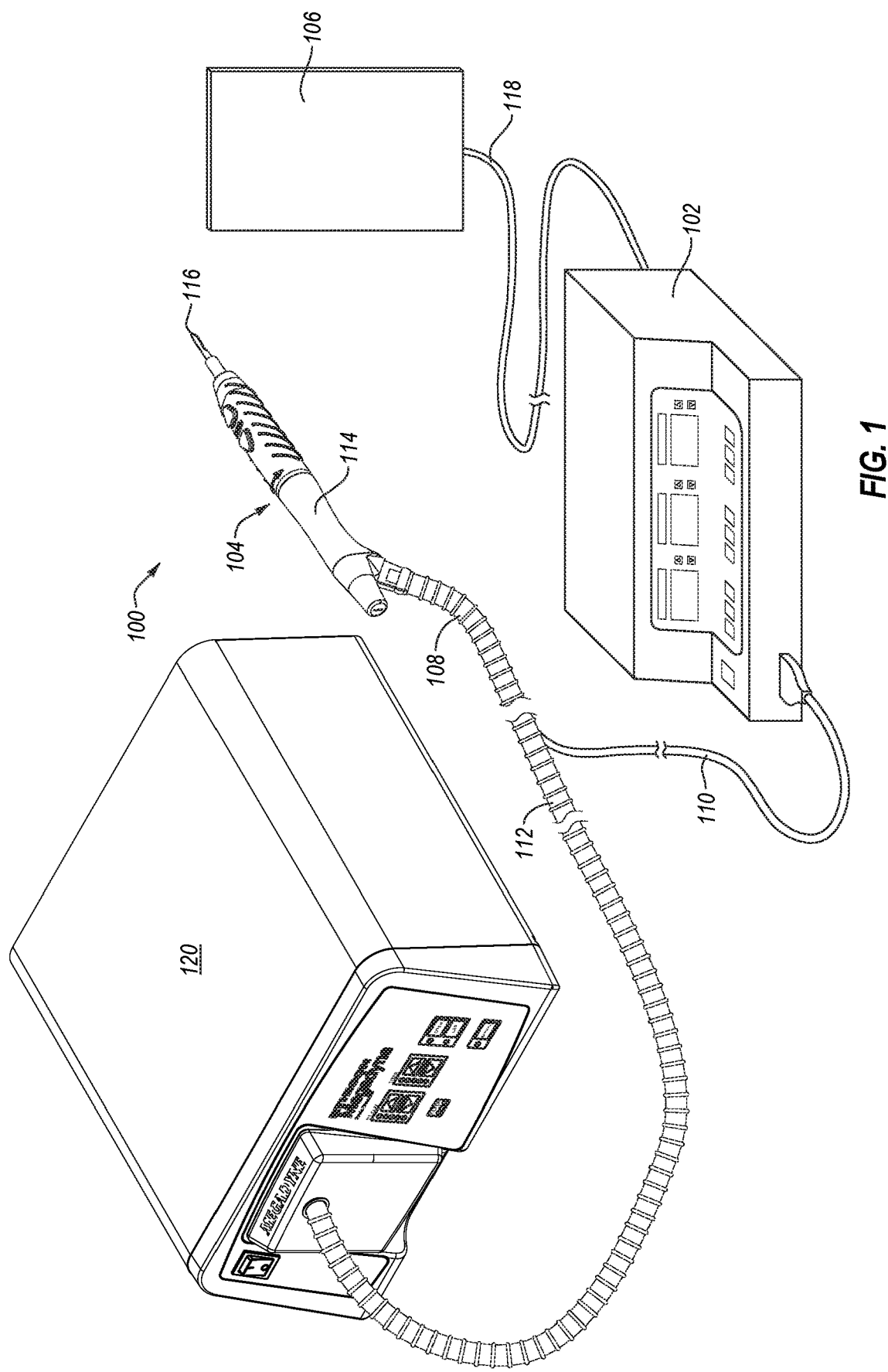
FIG. 1 illustrates an exemplary electrosurgical system.

The present disclosure relates to smoke evacuation systems associated with electrosurgical instruments and other hand-held instruments that produce smoke or cause smoke to be produced during use. FIG. 1, for example, illustrates an exemplary electrosurgical system 100. The illustrated embodiment includes a signal generator 102, an electrosurgical instrument 104, and a return electrode 106. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site and to, for example, a smoke evacuation system 120. In some embodiments, such as that illustrated in FIG. 1, cable 110 can extend through at least a portion of vacuum hose 112 and to electrosurgical instrument 104.

Generally, electrosurgical instrument 104 includes a hand piece or pencil 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with electrode tip 116. The heating takes place at an appropriately high temperature to allow electrosurgical instrument 104 to be used to perform electrosurgery. Return electrode 106 is connected to generator 102 by a cable 118 in order to complete the circuit and provide a return electrical path to wave generator 102 for energy that passes into the patient's body.

As explained in greater detail below, embodiments of electrosurgical instruments according to the present disclosure enable efficient capture of smoke generated during an electrosurgical procedure, such that smoke that is not immediately captured near the site of smoke generation (e.g., at the tissue/electrode tip interface) can still be captured and evacuated away from the operating environment. For example, vacuum suction originating from the smoke evacuation system 120 can draw the smoke into a conduit opening near the electrode tip 116, through the electrosurgical instrument 104, and through the vacuum hose 112 for processing at the smoke evacuation system 120.

Reference is made herein to the evacuation of smoke and components that facilitate such function. It will be appreciated that references to "smoke" is merely for simplicity and convenience, and is not intended to limit the disclosed and claimed embodiments to evacuation of only smoke. Rather, the disclosed and claimed embodiments may be used to evacuate substantially any type of fluid, including liquids, gases, vapors, smoke, or combinations thereof. Additionally, rather than simply evacuating fluid, it is contemplated that at least some of the embodiments may be used to deliver fluids to a desired location, such as a surgical site. As used herein, the term "fluid" includes bulk liquids and/or liquid vapor, which can include liquids—biologic in origin or otherwise—obtained from or introduced into a surgical site (e.g., water, saline, lymph, blood, exudate, pyogenic discharge, and/or other fluid). A "fluid" is additionally intended to include cellular matter or debris that is transported through a vacuum hose and into the fluid reservoir of a mechanically coupled fluid trap.

Smoke Evacuation System Fluid Traps

In some embodiments, a smoke evacuation system includes a fluid trap that directs smoke from a vacuum hose and into a filter and removes and collects at least a portion of the fluid content from the smoke. In some embodiments, the fluid trap includes an inlet port with an inlet body extending into an interior chamber of the fluid trap and oriented to initially direct incoming smoke into a bottom, interior chamber of the fluid trap. The fluid trap additionally includes an exhaust port for directing smoke from the interior chamber of the fluid trap to an area outside the fluid trap (e.g., into a filter associated with the smoke evacuation system). In some embodiments, the exhaust port is sized and shaped to mechanically couple to a smoke filter and can additionally, or alternatively, be sized and shaped to prevent the fluid trap from spilling its contents when, for example, the fluid trap is placed on a surface contacting the exhaust-port-side of the fluid trap.

In some embodiments, the fluid trap is sized and shaped to prevent spillage of stored fluid when the fluid trap is detached from the smoke evacuation system and positioned on a surface in any of a variety of different orientations. In some embodiments, the fluid trap includes a protrusion in a sidewall that increase the volume of the fluid reservoir of the fluid trap and which may additionally, or alternatively, prevent collected fluid from spilling when the fluid trap is positioned on a surface. Fluid traps disclosed herein can, in some embodiments, include a plurality of baffles or condensation surfaces to promote retention and/or extraction of fluid from smoke.

One or more embodiments beneficially enable identification of the relative or absolute fluid volume within the fluid trap, and in some embodiments, fluid traps can include visual or auditory indicators of the fluid level within the fluid trap. In some embodiments, the fluid trap can include a drain valve for quickly and/or easily accessing the contents of fluid trap and which can further enable emptying or draining the contents of the fluid trap. Beneficially, the fluid traps disclosed herein reduce the amount of fluid entering the filter or other components of smoke evacuation devices and safely retain such fluids collected by preventing or reducing the likelihood an inadvertent spill can occur. By reducing the total fluid content of the smoke and removing bulk liquid from the smoke, the usable life of mechanically coupled filters can be increased. Additionally, or alternatively, the reduced fluid content within the smoke can protect the electrical components within or associated with the smoke evacuation device.

Figure 2:
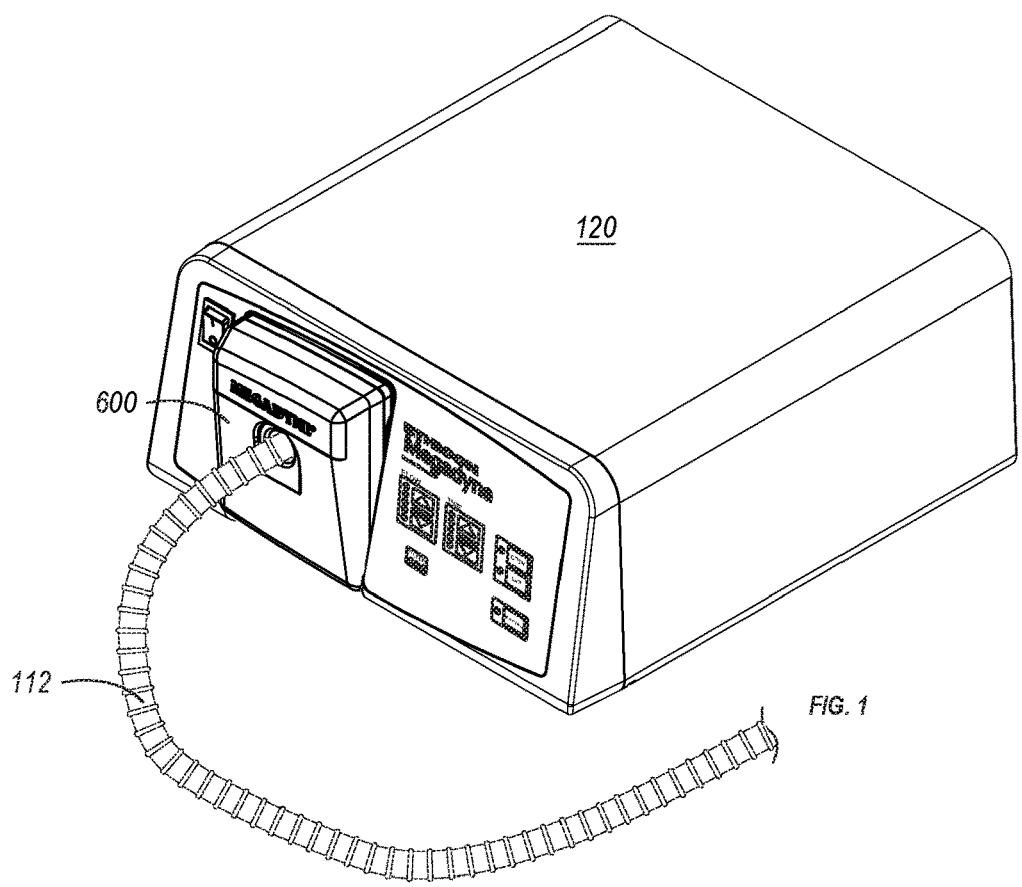
FIG. 2 illustrates a smoke evacuation system associated with an exemplary fluid trap.

Illustrated in FIG. 2 is the smoke evacuation system 120 of FIG. 1, and as shown, the smoke evacuation system 120 is coupled to a vacuum hose 112. The smoke evacuation system 120 is configured to produce suction and thereby draw smoke from the distal end of the vacuum hose 112 into the smoke evacuation system 120 for processing. Instead of the vacuum hose 112 being connected to the smoke evacuation system 120 through a smoke filter end cap (as shown in FIG. 1), the smoke evacuation system 120 of FIG. 2 is connected to the vacuum hose 112 through a fluid trap 600.

In some embodiments, the fluid trap 600 is a first smoke processing point that extracts and retains at least a portion of the fluid from the smoke before relaying the partially processed smoke to the smoke evacuation system 120 for further processing and filtration. The smoke evacuation system 120 beneficially enables smoke to be processed, filtered, or otherwise cleaned, reducing or eliminating unpleasant odors or other problems associated with smoke generation in the surgical theater (or other operating environment), and by extracting fluid from the smoke before it is processed by the smoke evacuation system 120, the fluid trap, among other things, increases the efficiency of the smoke evacuation system and increases the life of filters associated therewith.

Figure 3:
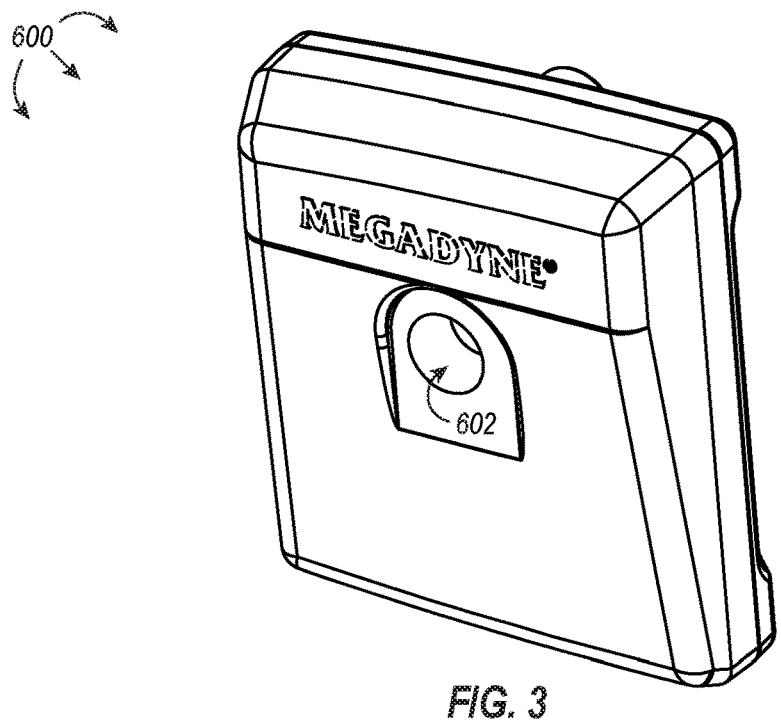
FIG. 3 illustrates a front perspective view of an exemplary fluid trap.
Figure 4:
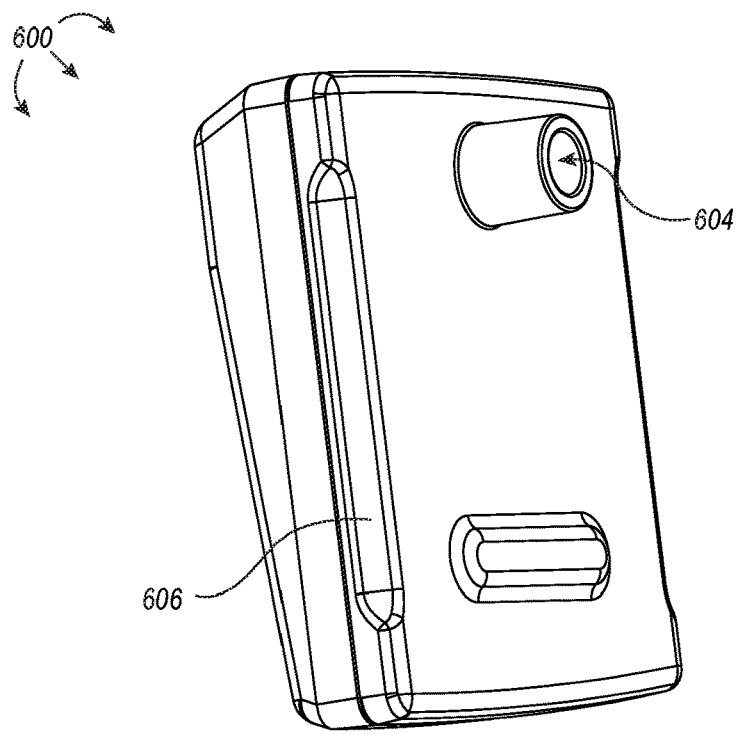
FIG. 4 illustrates a rear perspective view of the exemplary fluid trap of FIG. 3.
Figure 5:
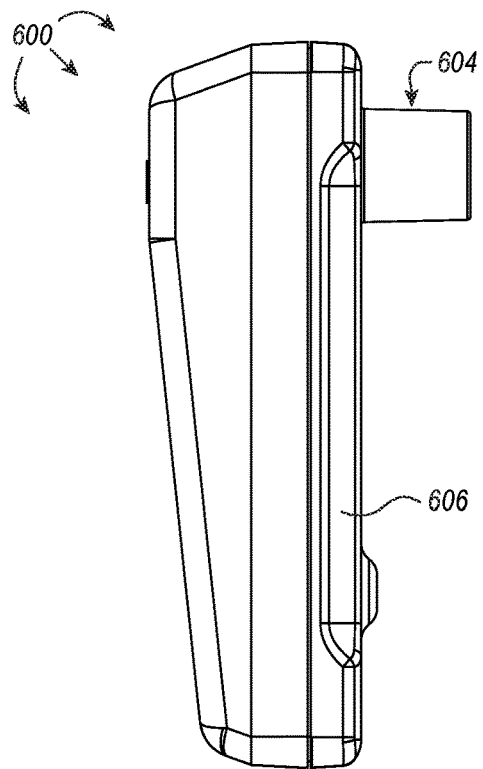
FIG. 5 illustrates a side view of the exemplary fluid trap of FIG. 3.

Referring now to FIGS. 3-5, illustrated are various views of a fluid trap 600 that is detached from or has yet to be associated with a smoke evacuation system, such as the smoke evacuation system 120 of FIG. 2. FIG. 3 illustrates a front perspective view of the fluid trap 600, and as shown, the fluid trap 600 includes an inlet port 602 that is defined by the front cover or surface of fluid trap 600. In some embodiments, the inlet port 602 is configured to releasably receive a vacuum hose. For example, an end of a vacuum hose can be inserted at least partially within the inlet port 602 and form an interference fit therewith. The interference fit can, in some embodiments, be a fluid tight and/or airtight fit so that substantially all of the smoke passing through the vacuum hose is transferred into the fluid trap 600. In some embodiments, other mechanisms of coupling or joining the hose with the inlet are employed such as, for example, a latch-based compression fitting, an O-ring, threadedly coupling the hose with the inlet, or other coupling mechanism known in the art.

A fluid tight and/or airtight fit between the vacuum hose and the fluid trap 600 can beneficially prevent fluids or other contents within the smoke from leaking at or near the junction of these two components. In some embodiments, the vacuum hose can be associated with the inlet port through an intermediate coupling device (e.g., an O-ring, adaptor, etc.) to further ensure an airtight and/or fluid tight connection between the vacuum hose and the fluid trap.

As shown in the rear perspective view of the fluid trap 600 illustrated in FIG. 4, the fluid trap 600 additionally includes an exhaust port 604 extending away from a rear cover or surface of the fluid trap 600. The exhaust port 604 defines an open channel between an interior chamber of the fluid trap 600 and the exterior environment. In some embodiments, the exhaust port 604 is sized and shaped to tightly associate with a smoke evacuation system or components thereof. For example, exhaust port 604 can be sized and shaped to associate with and communicate at least partially processed smoke from the fluid trap 600 to a smoke filter housed within smoke evacuation system 120. In some embodiments, the exhaust port extends away from a front, top, or side surface of the fluid trap.

In some embodiments, the exhaust port 604 includes or is spaced apart from the smoke evacuation system by a membrane (not shown). The membrane can act to prevent water or other liquid collected in the fluid trap from passing through the exhaust port and into the smoke evacuation system while permitting air, water vapor and/or evaporate to freely pass. For example, a high flow rate microporous polytetrafluoroethylene (PTFE) can be positioned downstream of the exhaust port and upstream of the smoke evacuation system components (e.g., a vacuum pump inlet) to protect the smoke evacuation system from damage and/or contamination.

Referring back to FIG. 4, fluid trap 600 can additionally include a gripping region 606 to assist a user in handling the fluid trap and/or connecting it with a vacuum hose and/or smoke evacuation system. The gripping region 606 is depicted as being an elongate recess. However, it should be appreciated that the gripping region 606, in some embodiments, can include a plurality of recesses or grooves, any of which can be sized and shaped to accommodate a user's digits or to otherwise provide a gripping surface. In some embodiments, the gripping regions are protrusions, rings, or tassels instead of recesses.

Referring now to FIG. 5, illustrated is a side view of the fluid trap 600 depicted in FIGS. 3 and 4. As shown, the front cover or surface of the fluid trap 600 is tapered from a wider upper region to a narrower lower region when viewing the fluid trap 600 in an upright position. In some embodiments, the front cover or surface does not taper, but rather, it maintains substantially uniform dimensions between the upper and lower regions of the fluid trap 600.

As also shown in FIG. 5, the exhaust port 604 is positioned proximate the upper end of the rear cover or surface of fluid trap 600 when the fluid trap 600 is viewed in an upright position. The inlet port 602 can be positioned substantially within the center of the fluid trap 600, as shown in the vertical cross-section of the fluid trap 600 depicted in FIG. 6, or it can be positioned higher or lower along the front surface. In some embodiments, the inlet port is positioned laterally off-center and/or proximate an outer edge of the front cover or surface. The respective positioning of the exhaust port 604 can mimic the lateral and/or vertical positioning of the inlet port, but in some embodiments, the exhaust port 604 remains in the position shown in FIGS. 2-6 so that its placement does not functionally impair the fluid trap 600 from associating with the smoke evacuation system 120 (or components thereof).

Figure 6:
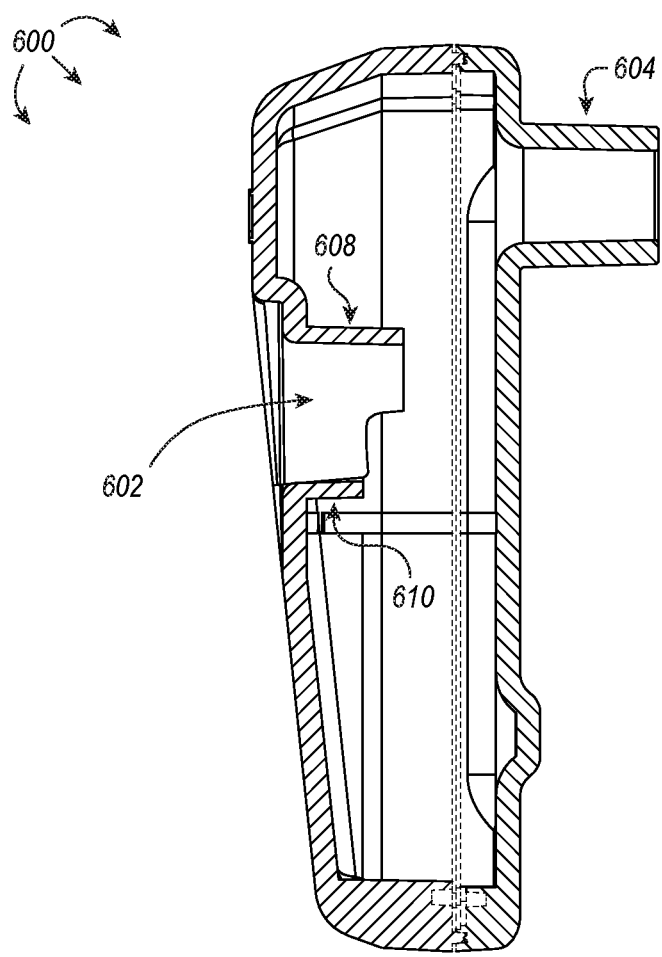
FIG. 6 illustrates a vertical cross-section of the exemplary fluid trap depicted in FIG. 5.

With continued reference to FIG. 6, the inlet port 602 is defined by a notched cylindrical body that extends into the interior chamber of the fluid trap 600. The notched cylindrical shape of the inlet port 602 is defined by an upper sidewall 608 and a lower sidewall 610. The upper sidewall 608 extends into the interior chamber of the fluid trap 600 farther than the shorter, lower sidewall 610 such that a cross-sectional slice transecting the longitudinal axis of the inlet port 602 yields a circle (or similar arcuate shape) where the cross-section includes both the upper and lower sidewalls 608, 610, and a cross-sectional slice transecting the longitudinal axis of the inlet port 602 yields a semi-circle where the cross-section includes only that portion of the upper sidewall 608 that extends beyond the lower sidewall 610.

As also shown in FIG. 6, the exhaust port 604 is positioned above the inlet port 602. In some embodiments, the exhaust port 604 is positioned lower on the rear cover of the fluid trap 600 than what is illustrated in FIGS. 4-6. In such embodiments, the exhaust port 604 is preferentially positioned above an associated inlet port 602. As used herein, the relative positioning of the exhaust port being "above" the inlet port or the inlet port being positioned "below" the exhaust port is intended to preferentially include embodiments where any portion of the openings defined by the inlet port and exhaust port, respectively, are in different horizontal planes. Additionally, in some embodiments, the exhaust port is understood to be "above" the inlet port when the exhaust port is more proximate an upper edge or surface of the fluid trap than the inlet port and/or the inlet port is more proximate a lower edge or surface of the fluid trap than the exhaust port. Additionally, the exhaust port can be "above" the inlet port if a portion of the respective openings (e.g., less than 50%, less than 40%, less than 30%, less than 20%, less than 10%, less than 5%, etc.) coexist within the same horizontal plane (or sets of horizontal planes) but there is at least one horizontal plane that includes an upper surface of the exhaust port that does not include any portion of the inlet port.

In some embodiments, the relative positioning of the inlet port 602 and the exhaust port 604 promote extraction and retention of fluid from the smoke as it passes into the fluid trap 600. In some embodiments, the notched cylindrical shape of the inlet port 602 can beneficially act to initially direct smoke and the accompanying airflow towards a fluid reservoir of the fluid trap 600 or otherwise directionally away from the exhaust port. Such an exemplary airflow is depicted in FIG. 7.

As shown, smoke enters the fluid trap 600 through inlet port 602 (illustrated by arrow A) and exits the fluid trap through exhaust port 604 (illustrated by arrow E). At least partially due to the geometry of the inlet port (e.g., a longer, upper sidewall 608 and a shorter, lower sidewall 610), the smoke entering the inlet port 602 is initially directed downward into the fluid reservoir of the fluid trap 600 (illustrated by arrows B). As smoke continues to be pulled into the fluid trap 600 along arrows A and B, the smoke that was initially directed downward tumbles and is directed laterally away from its source to travel in an opposite but parallel path towards the upper portion of the fluid trap 600 and out of the exhaust port 604 (illustrated by arrows D and E).

Figure 7:
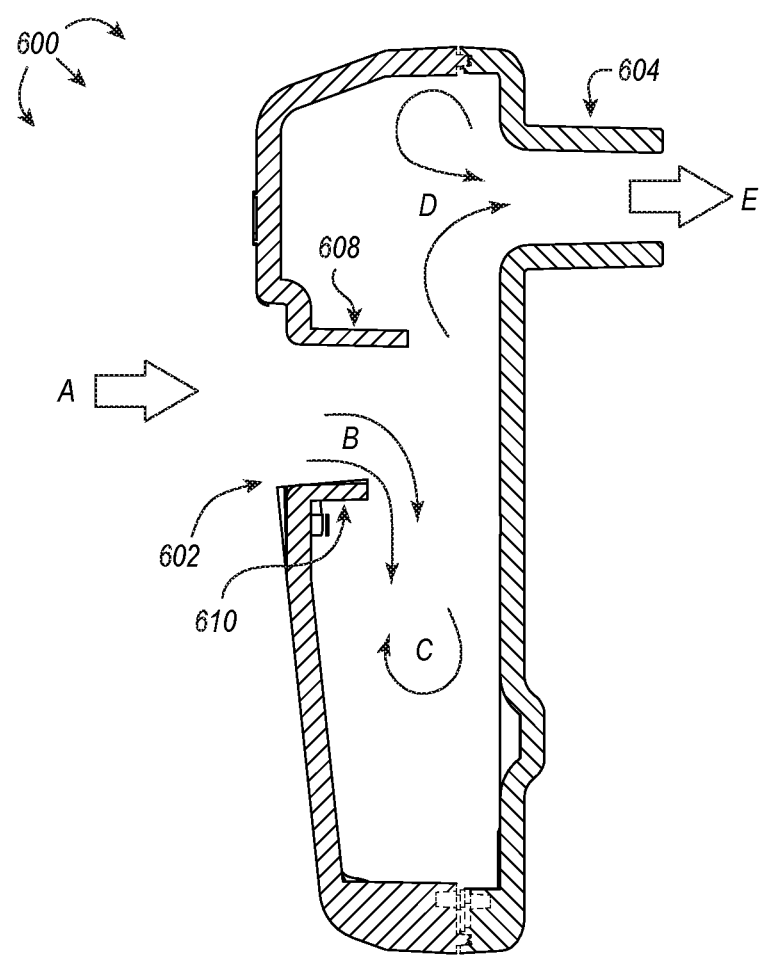
FIG. 7 illustrates a simplified vertical cross-section of the exemplary fluid trap depicted in FIG. 5 and an embodiment of air flow through therethrough.

In some embodiments, the directional flow of air/smoke through the fluid trap 600 (as illustrated in FIG. 7, for example) enables fluids within the smoke to be extracted and retained within the lower portion of the fluid trap 600. Further, the relative positioning of the exhaust port 604 with respect to the inlet port 602 discourages liquid from inadvertently being carried through the exhaust port 604 by the flow of smoke while not substantially hindering airflow into and out of the fluid trap 600. Additionally, the configuration of the inlet and exhaust ports 602, 604 and/or the size and shape of the fluid trap, itself, can enable the fluid trap 600 to be spill resistant.

For example, in an upright position, fluid 612 that is extracted from smoke is retained within the bottom portion of the fluid trap 600, as shown, for example, in FIG. 8. If the fluid trap 600 falls or is moved or its orientation changed from an upright position such that it becomes oriented on a surface inlet port side down, as shown in FIG. 9, the fluid trap 600 can still retain the fluid 612 within the interior chamber owing to its size and shape. For example, the upper sidewall 608 and the lower sidewall 610 of the inlet port 602 protrude deep enough into the interior chamber of the fluid trap 602 to create a front cover volume that is bounded by the surface area of the interior surface of the front cover and the sidewalls 608, 610 of the inlet port 602.

It should be appreciated that although the fluid 612 in FIG. 9 appears to be separated into two distinct portions, FIG. 9 illustrates a cross-sectional view of the fluid trap 600. As described above, the inlet port 602 can be defined by a notched cylindrical sidewall (or cylindrical sidewall) that does not transact the entire front cover or surface. Accordingly, when the fluid trap 600 is positioned on a surface with the inlet side down, as shown in FIG. 9, fluid 612 can pass around the intrusive sidewalls of inlet 602 and be distributed along the interior surface of the cover. Accordingly, in some embodiments, the front cover of the fluid trap is dimensioned such that the volume of the front cover is equal to or greater than the maximum fluid volume of the fluid reservoir. The volume of the front cover can, for example, be calculated as the product of the surface area of the front cover and the average depth of the front cover with respect to the lowest intrusive sidewall of the inlet port. In some embodiments, the maximum volume of the fluid reservoir is determined by the volume of the front cover. As used herein, a "fluid reservoir" includes a subset of the interior chamber of the fluid trap, particularly the interior volume of the fluid trap defined by the interior sidewalls of the fluid trap below the inlet port.

In some embodiments, the fluid trap 600 can be considered full when the volume of fluid 612 contained therein rises as high as the terminal end of the lower sidewall 610 when the fluid trap is positioned on a surface with the inlet side down (i.e., at a maximum front cover volume). In some embodiments, the fluid trap 600 can be considered full when the volume of fluid 612 contained therein rises a particular distance below the terminal end of the lower sidewall 610 when positioned on the surface with the inlet side down. In some embodiments, the foregoing particular distance is about 1/16", 1/8", about 1/4", about 3/8", about 1/2", about 5/8", about 3/4", about 7/8", or about 1".

In some embodiments, the fluid trap 600 is additionally spill resistant owing at least partially to its size and shape when oriented on a surface with the exhaust port side down, as shown in FIG. 10. The sidewalls defining the exhaust port 604 extend a length 616 away from the rear surface of the fluid trap 600 such that the exhaust port acts like a kickstand to stably support the fluid trap 600 in an inclined position, directing the fluid 612 away from the exhaust port 604. As shown in FIG. 10, the fluid 612 is retained within the fluid reservoir of the fluid trap 600 and at least partially along the rear cover of the fluid trap. The fluid 612 is retained within the fluid trap 600 when the fluid trap is oriented exhaust port 604 side down because, in some embodiments, the rear cover volume is greater than the volume of fluid 612 contained therein. The rear cover volume can, in some embodiments, be calculated as the volume of the interior chamber defined by the interior sidewalls of the fluid trap that is bounded by a line tangent to a lowest interior-facing sidewall of the exhaust port and parallel with the surface upon which the exhaust port lies. In some embodiments, the line parallel with the surface upon which the exhaust port lies is a line normal to the force of gravity.

In some embodiments, the volume of the rear cover is expanded by a protrusion or protruding sidewall 618. The protruding sidewall 618 can be sized proportionally with the length 616 of the exhaust port 604, or it can have defined dimensions regardless of the length 616 of the exhaust port 604. For example, in embodiments where the protruding sidewall 618 is sized proportionally with the length 616 of the exhaust port 604, as the length 616 of the exhaust port 604 decreases, the angle of incline experienced by the fluid trap 600 can similarly decrease. A decreased incline causes a decreased rear cover volume. By increasing the width or depth of the protrusion 618, the protrusion 618 effectively increases the rear cover volume. Alternatively, as the length 616 of the exhaust port 604 increases, the angle of incline experienced by the fluid trap 600 can similarly increase. The increased incline causes an increase in the rear cover volume. The protrusion 618 can be proportionally shrunk or removed as the rear cover volume increases to prevent fluid 612 from spilling out of the exhaust port 604.

It should be appreciated that in some embodiments, the fluid reservoir volume can additionally be increased by the same protrusion 618 shown in at least FIGS. 8-10 (or a different protrusion). For example, an increase in the size of the protrusion 618 can proportionally increase the fluid reservoir volume, and a decrease in the size of the protrusion 618 can proportionally decrease the fluid reservoir volume. Additionally, although the protrusion 618 is shown in at least FIGS. 8-10 as being located on the rear cover, a protrusion may additionally, or alternatively, be located on the front cover.

In some embodiments, the fluid trap 600 can be considered full when the volume of fluid 612 contained therein rises as high as but not into the exhaust port 604 when the fluid trap is positioned on a surface with the exhaust port 604 side down (i.e., at a maximum rear cover volume).

As described above with respect to at least FIGS. 8-10, embodiments of the present disclosure include fluid traps that are spill resistant. In such embodiments, the maximum volume of fluid that can be extracted and retained while maintaining the fluid trap's spill resistant feature is dependent upon the volume of the fluid reservoir of the fluid trap, the volume of the front cover, and the volume of the rear cover. In some embodiments, the maximum volume is the lesser of the fluid reservoir volume, the front cover volume, and the rear cover volume. For example, in some embodiments, the front cover volume is less than the fluid reservoir volume and the rear cover volume. Accordingly, the maximum volume for the foregoing exemplary fluid trap is at most the front cover volume.

Figure 11:
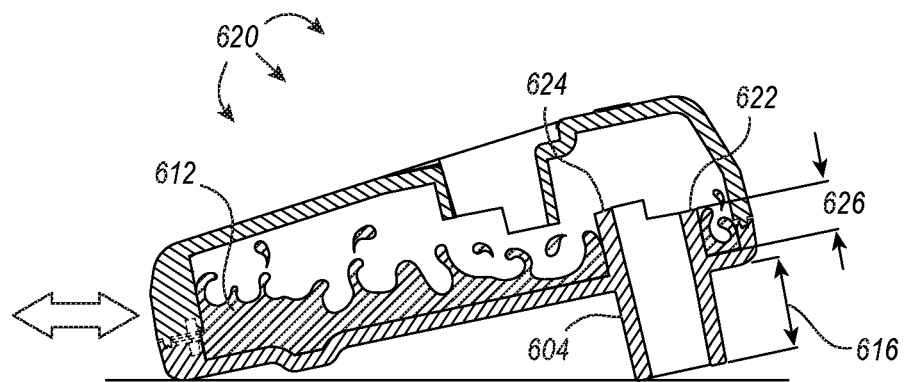
FIG. 11 illustrates a simplified vertical cross-section of another exemplary fluid trap having fluid collected therein that is positioned on a surface inlet-side up with the fluid shown as being agitated.

Referring now to FIG. 11, the exhaust port 604 can be adapted to include upper and lower sidewalls 622, 624 that extend into the interior chamber of the fluid trap 620. The upper and lower sidewalls 622, 624 can similarly form a notched cylinder (as described above with respect to upper and lower sidewalls 608, 610 of the inlet port 602). Alternatively, the upper and lower sidewalls of the exhaust port can define a cylindrical channel. Regardless, by extending upper and lower sidewalls 622, 624 of the exhaust port 604 into the interior chamber of the fluid trap 620, the fluid trap 620 becomes more resistant to spilling or at least reduces the likelihood that splashes or sloshing of the fluid 612 inside the fluid trap 620 results in spillage when the fluid trap 620 is positioned on a surface inlet side up—even when agitated. In some embodiments, extending upper and lower sidewalls 622, 624 into the interior chamber of the fluid trap 620 may also allow for a shorter exterior length 616 of the exhaust port 604 without appreciably risking spilling liquid 612. In some embodiments, the length 626 of the upper sidewall 622, which is shorter than the lower sidewall 624 in some embodiments, can be proportional to the length 616 of the exhaust port 604. For example, the length 626 of the upper sidewall 622 can increase to compensate for a decreased length 616 of the exhaust port 604. Similarly, as the length 616 of the exhaust port 604 increases, the length 626 of the upper sidewall 622 can decrease.

In some embodiments, the exhaust port 604 protrudes into the interior chamber of the fluid trap 620, as illustrated in FIG. 11. This can, in some embodiments, decrease the likelihood that fluid can freely or accidentally transit between the inlet 602 and the exhaust 604. In some embodiments, having the exhaust port protrude into the interior chamber of the fluid trap increases the rear cover volume. Additionally, or alternatively, the exhaust port 604 protrudes into the interior chamber of the fluid trap 620 with the lower sidewall 624 being longer than the upper sidewall 622 so as to further manipulate the airflow through the fluid trap 620. As it should be appreciated, the configuration of sidewalls having a staggered length, as shown in FIG. 11, can increase the flow rate of air or smoke proximate the upper sidewall 622 (similar to the flow described above for inlet port 602).

Figure 12:
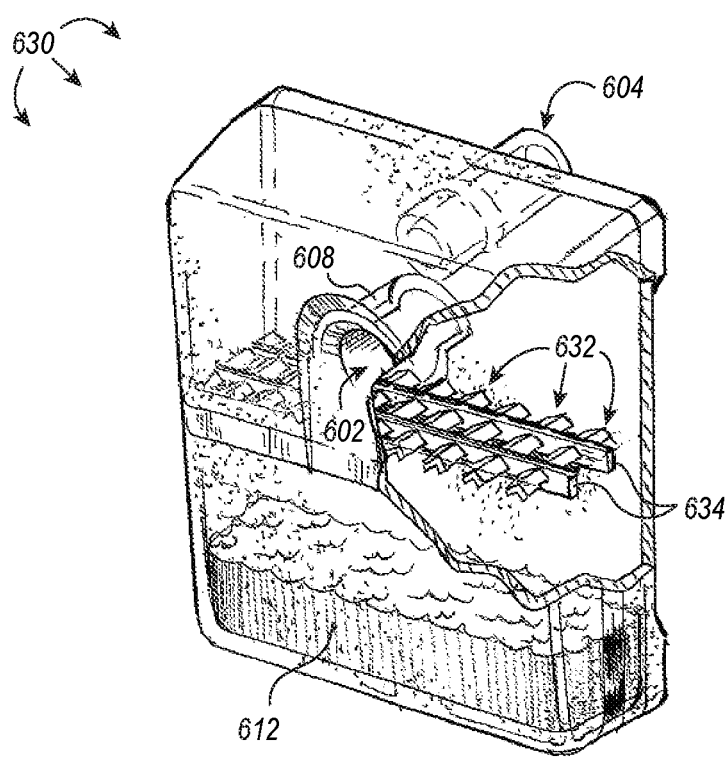
FIG. 12 illustrates a partial cross section, perspective view of a fluid trap having baffles.

In some embodiments, it may be advantageous to include physical barriers within the fluid trap to reduce the likelihood that splashes or sloshing of the fluid inside the fluid trap results in spillage. Referring now to FIG. 12, illustrated is a partial cross-section, perspective view of a fluid trap 630 having a plurality of baffles 632 disposed within an interior chamber thereof. The plurality of baffles 632 can be disposed along baffle securing members 634, as shown in FIG. 12. The baffle securing member 634 can attach to one or more interior surfaces of the fluid trap 630 and act to hold the plurality of baffles 632 stationary. In some embodiments, the baffles, themselves, are attached to one or more interior surfaces of the fluid trap, and the baffles securing members can be optionally omitted.

As illustrated by FIG. 12, smoke can enter inlet port 602 and be similarly directed downward owing to the shorter, lower sidewall 610 and the longer, upper sidewall 608 that form a notched cylindrical projection (as discussed above with respect to at least FIG. 7). Accordingly, liquid within the smoke can be directed to the fluid reservoir of the fluid trap 630 along angled baffles 632. Once the liquid 612 passes beneath the baffles 632, the angled arrangement of the baffles 634 acts to catch upward moving splashes or droplets and redirect them down towards the fluid reservoir. In such a manner, the plurality of baffles can minimize fluid motion during handling of the fluid trap 630. In some embodiments, the angled baffles 634 can additionally act as condensation surfaces to promote the condensation of liquid vapor in the smoke, which is similarly directed towards the interior chamber of the fluid trap 630 after condensing into droplets (not shown). In some embodiments, the baffles are made of absorptive material and can act to wick fluid from the smoke.

Figure 13:
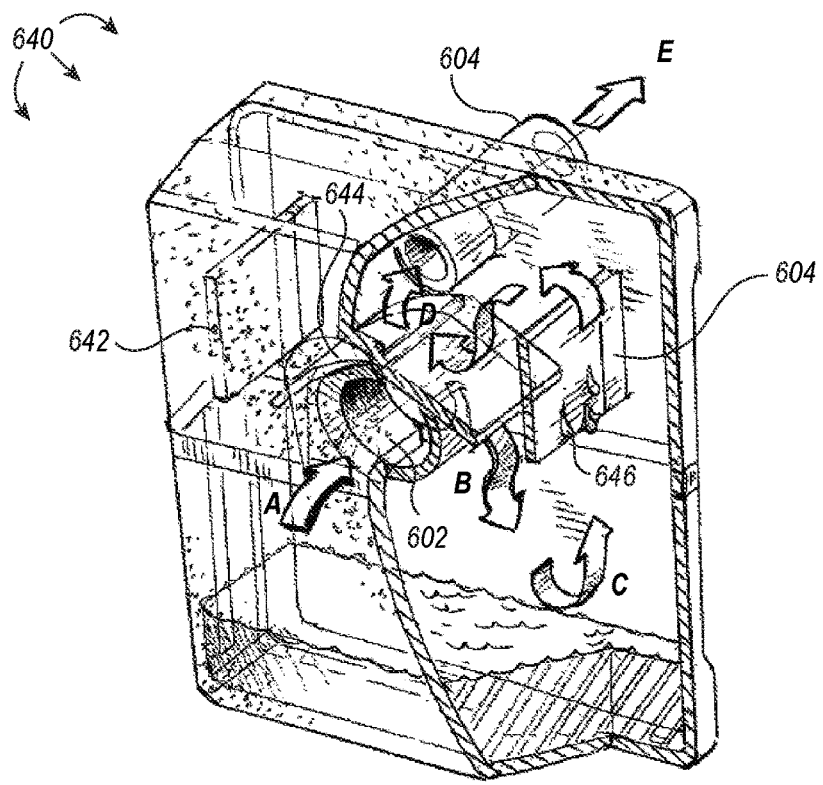
FIG. 13 illustrates a partial cross section, perspective view of a fluid trap having a plurality of interior condensation surfaces.

In some embodiments, additional measures can be taken to reduce and/or control aerosols and small droplet fluids that are moving at higher velocities by, for example, removing them from the airflow path. Referring now to FIG. 13, illustrated is a fluid trap 640 that includes a splash canopy 644 positioned within the collection chamber of the fluid trap 640, above the inlet port 602 and providing a physical barrier between the exhaust port 604 and the inlet port 602. As shown in FIG. 13, the splash canopy 644 spans the interior sidewall of the front cover to the interior sidewall of the rear cover and extends laterally across and past the width of the inlet port 602. In some embodiments, the splash canopy is attached to the sidewall of the rear cover, extends over the upper sidewall of the inlet port and towards the interior sidewall of the front cover but does not attach thereto.

The splash canopy 644 is also illustrated as having a downwardly concave arcuate shape. Additionally, or alternatively, the splash canopy can be planar and/or extend over the width of the inlet port. In some embodiments, the contour and position of the splash canopy 644 can advantageously act to direct incoming airflow (shown by arrow A) and any splashing fluid downward toward the bottom, interior chamber of the fluid trap 640 (shown by arrow B). Similar to the airflow described above with respect to FIG. 7, the downwardly directed air can flow laterally and upward (shown by arrow C) where it passes over and around a vertically oriented splash wall 642. As shown in FIG. 13, the splash wall 642 can span the distance between the interior sidewall of the front cover to the interior sidewall of the rear cover and can extend vertically a distance from at least the lower terminal edge of the splash canopy 644 (or lower) to the bottom of the exhaust port 604.

In some embodiments, the vertical distance spanned by the splash wall 642 can be different. For example, the splash wall can begin at a point coplanar to the bottom of the inlet port and extend vertically upward, terminating in at a point coplanar with the top of the splash canopy, the bottom of the exhaust port, or the top of the exhaust port. Additionally, as shown in FIG. 13, the splash wall 642 can be spaced apart from the splash canopy 644. However, in some embodiments, the splash canopy and the splash wall are connected to form a W-shaped or U-shaped splash wall that partially surrounds the exhaust port 604.

In some embodiments, the splash canopy 644 and/or the splash wall 642 can include or be made of a fibrous fluid wicking material (e.g., glass borosilicate or similar) which can enable the splash canopy 644 and/or splash wall 642 to remove aerosols and small droplet fluids from the inbound smoke. In some embodiments, the splash walls 642 and/or the splash canopy 644 can act as condensation promoting surfaces where aerosols and small droplets of fluids can condense and accumulate into droplets 646 that fall into the bottom, interior chamber.

In some embodiments, the fluid trap contains a plurality of splash walls and/or splash canopies, which can be tiered, stacked, or aligned in series. In some embodiments the splash walls and splash canopies are made of or include heat conductive materials that promote condensation.

Figure 14:
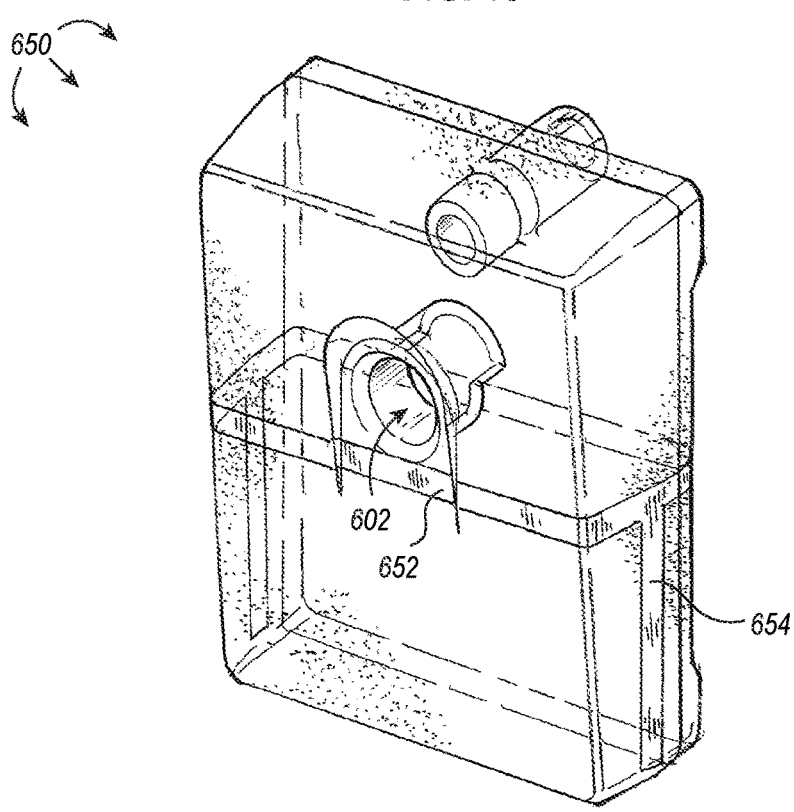
FIG. 14 illustrates a perspective view of a fluid trap with transparent viewing windows.

In some embodiments, it may be advantageous to monitor the total volume of fluid collected within the fluid trap. As shown in FIG. 14, a fluid trap 650 can include a horizontal viewing window 652 and/or a vertical viewing window 654. The viewing windows 652, 654 can be an integral part of the fluid trap sidewalls. As shown in FIG. 14, the horizontal viewing window 652 can wrap circumferentially around fluid trap 650 at a position below the inlet port 602. The positioning of the horizontal window may, in some embodiments, indicate a maximum fill line for the fluid reservoir 650. Alternatively, a plurality of horizontal viewing windows can be positioned along the fluid trap (e.g., in tiers) so the volume of fluid within the fluid trap can be progressively monitored and/or observed. Additionally, or alternatively, the vertical viewing window 654 can join with one or more horizontal viewing windows at at least one point and extend to the bottom of the fluid trap 650, as illustrated in FIG. 14.

Although illustrated as being positioned on a side of the fluid trap 650, it should be appreciated that the vertical viewing window 654 may be positioned on a front surface and/or rear surface of the fluid trap 650. In some embodiments, placing the horizontal and/or vertical viewing windows on the front surface can beneficially enable a user to quickly identify the volume level of fluid contained within the fluid trap without disassociating or otherwise removing the fluid trap from the smoke evacuation system. In some embodiments, the viewing windows are made of a transparent and/or translucent material that allow a user to readily view the contents of the fluid trap through the viewing window. For example, the viewing window may include glass or plastic, or in some embodiments, the viewing window may include frosted glass or plastic to better indicate dark blood within the fluid trap.

Figure 15:
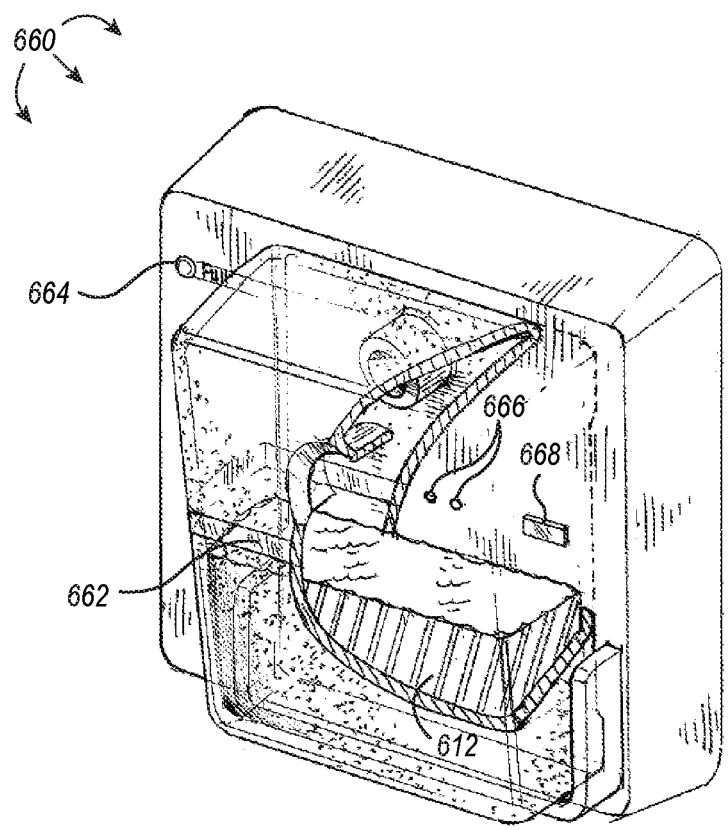
FIG. 15 illustrates a partial cross section, perspective view of a fluid trap having a fill detector and indicator light.

In some embodiments, a visual indicator coupled to a sensor can additionally, or alternatively, indicate the amount or volume of fluid within the fluid trap. For example, as shown in FIG. 15, the fluid trap 660 includes a horizontal viewing window 662 that indicates a maximum fill line for the fluid trap 660. The fluid trap 660 additionally includes an optical emitter and detector pair 666 positioned at or adjacently below the maximum fill line. The emitter and detector pair 666 can beneficially identify via optics whether fluid 612 within the fluid trap 660 has risen to a level at or above the emitter and detector pair 666. Upon determining that fluid 612 is at or above the level of the emitter and detector pair 666, an electrical signal can be sent to activate a status light 664 that indicates the fluid trap 660 is full.

Additionally, or alternatively, the fluid trap 660 can include an ultrasonic detector 668 that identifies a change in signal and causes an electrical signal to be sent to activate the status light 664, indicating the fluid trap 660 is full. For example, an identified change in signal can include the ultrasonic signal being consistently received at the ultrasonic detector 668 more quickly than previously observed. As an additional example, an identified change in signal can include the ultrasonic signal being received at the ultrasonic detector 668 within a threshold time that is indicative of the ultrasonic waves passing through a liquid medium.

Figure 16:
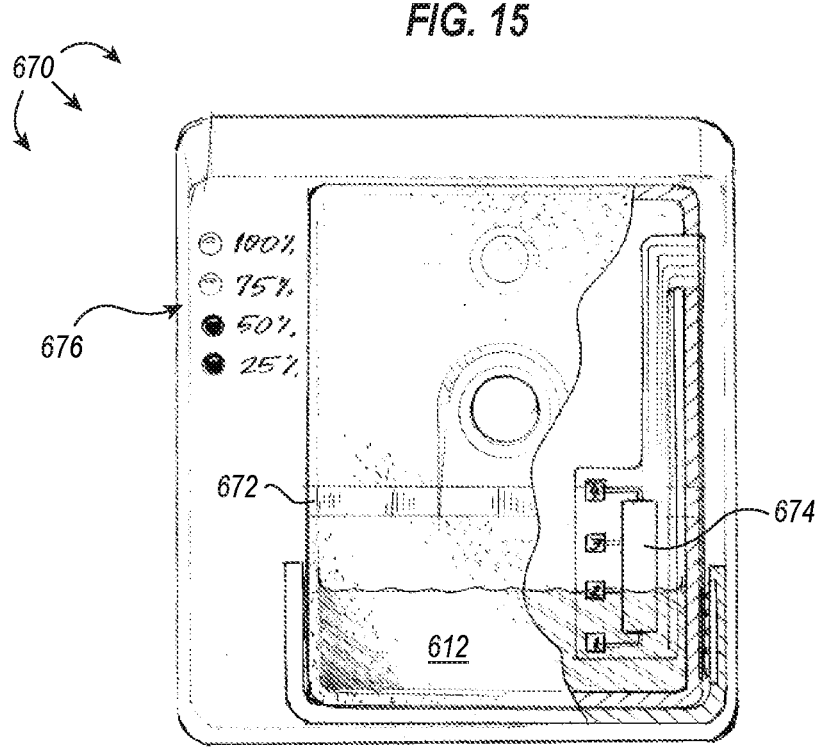
FIG. 16 illustrates a partial cross section, front view of a fluid trap having a graded fill sensor and indicator light.

In some embodiments, the volume of fluid within a fluid trap can be progressively monitored and/or indicated electronically, as shown, for example, in FIG. 16. The fluid trap 670 of FIG. 16 includes a resistive strip 674 having a plurality of nodes that are sequentially activated upon detection of liquid at the node. Each node of the resistive strip 674 can correspond to one or more status lights 676 such that upon activation of each node on the resistive strip, the corresponding status light is activated. For example, as shown in FIG. 16, the fluid level 612 is activating nodes 1 and 2, and the corresponding status lights—25% and 50% respectively—are turned on. In some embodiments, one of the nodes on the resistive strip can correspond to an audio signal or alarm that provides an audible cue—in addition to or separate from the visual cue(s) provided by the status light(s)—that the fluid trap is full and needs to be replaced or drained.

Although the embodiment of FIG. 15 is illustrated as having a single optical emitter and detector pair and a single ultrasonic detector, it should be appreciated that in some embodiments, a fluid trap can include a plurality of optical emitter and detector pairs and/or a plurality of ultrasonic detectors—and in any combination—to achieve an analogous progressive status light activation corresponding to the amount of fluid within the fluid trap like that depicted and described in FIG. 16.

Figure 17:
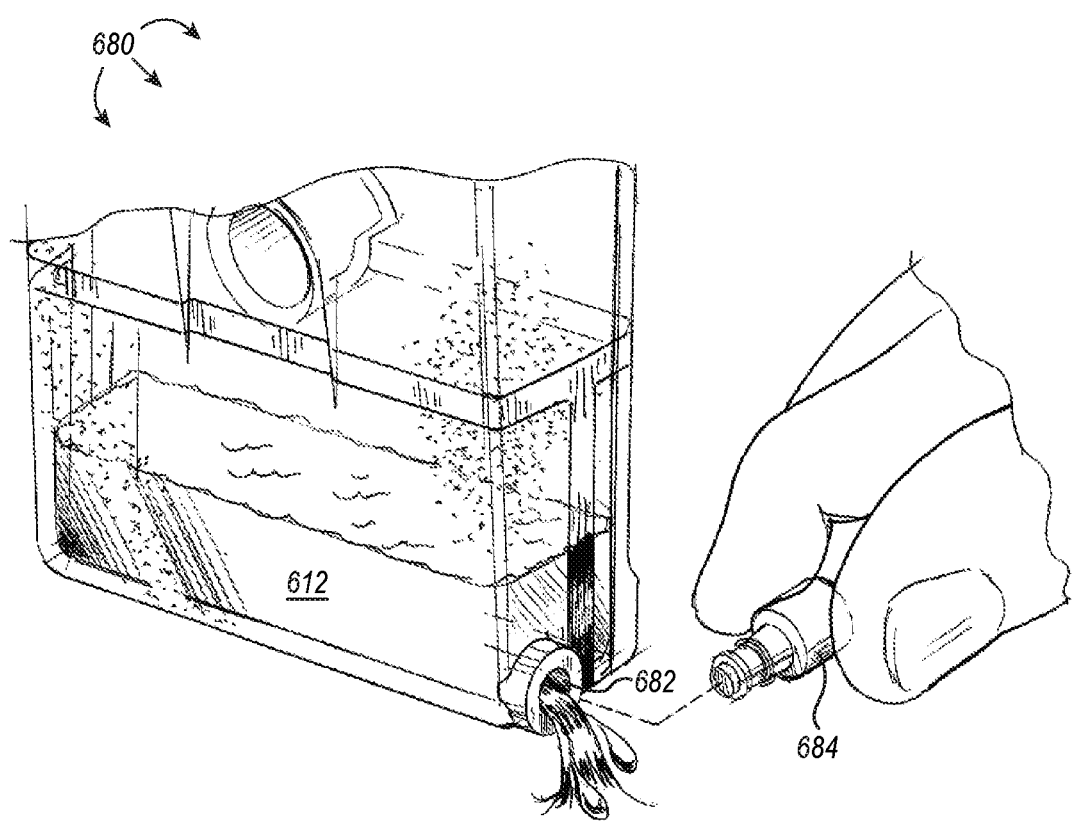
FIG. 17 illustrates a partial perspective view of a fluid trap with a drain valve.

In some embodiments, upon an indication that the fluid trap is full, the fluid trap is discarded. Alternatively, the fluid can be drained from the fluid trap for continued use. For example, as shown in FIG. 17, a fluid trap 680 can include a drain 682 for draining fluid 612 from the fluid trap 680. The drain 682 can be associated with a removable drain plug 684, as shown in FIG. 17, or alternatively, the drain can include a lever or valve for opening and/or closing the drain. The drain 682 may be positioned at a lower side edge of the fluid trap 660, or in some embodiments, the drain may be positioned on the lower front face of the fluid trap. In some embodiments, it is advantageous for the drain to be located near the bottom of the fluid trap so that opening the drain (e.g., by removing a drain plug or opening a drain valve) causes immediate drainage of fluid from the fluid trap. In other embodiments, however, it may be advantageous to position the drain near the top of the fluid trap so that opening the drain does not immediately cause fluid to be expelled. Instead, a user can pour the fluid at a rate that is more easily controlled by the user.

Filter Medium Compression Systems

In some embodiments, after at least a portion of a fluid has been removed from the smoke using fluid traps (as described above), the partially processed smoke can be further filtered within the smoke evacuation system 120 (as illustrated, for example, in FIG. 2). Alternatively, in some embodiments, smoke is transferred directly from the vacuum hose 112 into the smoke evacuation system 120 (as shown, for example, in FIG. 1). Regardless of whether the smoke is preprocessed at a fluid trap or directly transferred to the smoke evacuation system 120 from vacuum hose 112, a smoke filter (e.g., smoke filter 700 illustrated in FIG. 18) can be used to remove particulate matter and gaseous pollutants from the smoke.

However, it can be difficult to process and/or filter smoke, as it can contain particulate matter of various sizes, volatile organic compounds, water vapor, and potentially other noxious chemicals and compounds. Traditionally, particulate matter can be removed from smoke using particulate filters, which have a wide range of airflow resistance and efficiency. For example, coarse media filters, which broadly include low air resistant filters such as fiberglass, polyester, and pleated filters, can be used to remove the majority of large particulate matter (e.g., greater than 10 µm). In some instances, coarse media filters can be used to remove at least 85% of large particulate matter (e.g., greater than 10 µm) and between 50%-95% of small particulate matter (e.g., between 1-3 µm). Some coarse media filters can remove greater than 95% of small particulate matter.

High efficiency particulate air (HEPA) filters and ultra-low penetration air (ULPA) filters can be used for filtering fine particulate matter. HEPA filters, for example, are defined by the U.S. Department of Energy as filters capable of removing at least 99.97% of airborne particulate matter up to 0.3 µm in diameter. HEPA filters typically have a minimal airflow resistance compared to the higher efficiency ULPA filters. Although ULPA filters are typically associated with higher airflow resistance, ULPA filters are generally more efficient at filtering fine particulate matter. Most ULPA filters can remove at least 99.9995% of airborne particulate matter up to 0.12 µm in diameter.

Particulate filters are, for the most part, not very effective at removing other contaminants, particularly those gaseous pollutants found within smoke like volatile organic compounds. Sorbent-based filters can remove a number of gaseous pollutants from air and smoke, including volatile organic compounds, by chemically cross-linking the gaseous pollutant to the surface of the sorbent, and because adsorption is dependent upon the surface area of the sorbent, activated carbon is an ideal sorbent. Activated carbon is highly microporous and offers a significant amount of surface area per unit volume.

Filters employing sorbents like activated carbon require surface exposure of the air or smoke to be filtered with the sorbent in order for adsorption to occur. As it can be appreciated, therefore, the amount of surface area exposed to the air or smoke to be filtered is generally proportional to the amount or efficiency of filtration, and it is desirable to limit any gaps or routes through a sorbent-based filter that minimize surface area exposure thereto.

Figure 18:
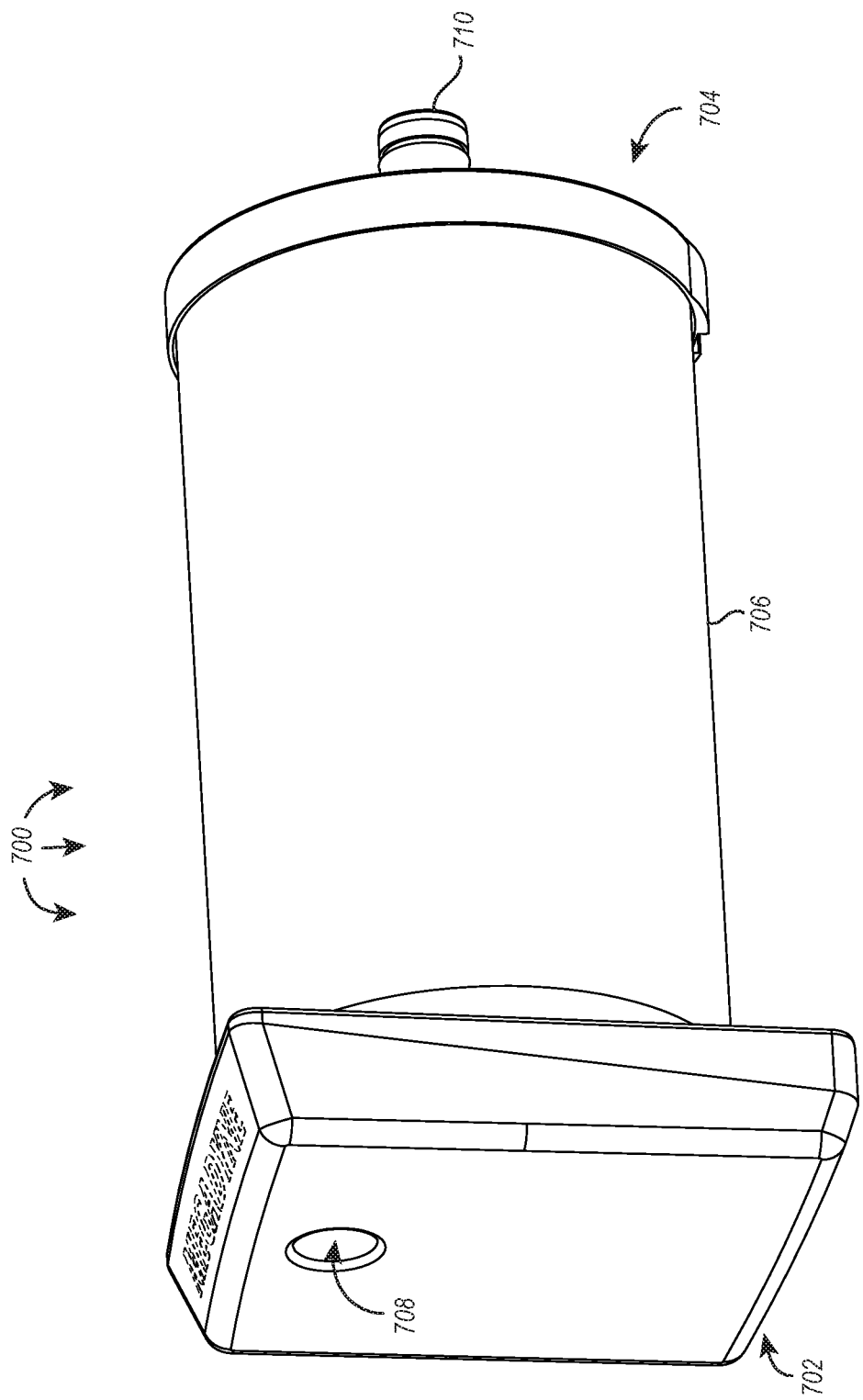
FIG. 18 illustrates an exemplary smoke filter for use with a smoke evacuation system.

Referring now to FIG. 18, illustrated is a smoke filter 700, which can be used with smoke evacuation systems disclosed herein. The smoke filter 700 includes a front cap 702 and a back cap 704 and a filter body 706 disposed of therebetween. As shown, the front cap 702 can include a filter inlet 708, which in some embodiments, receives smoke directly from a vacuum hose or other smoke source, or alternatively, the smoke inlet may associate with a fluid trap exhaust port to communicate partially processed smoke into the smoke filter 700. In some embodiments, the front cap 702 is replaced by a fluid trap that communicates smoke directly from the smoke source, and after removing at least a portion of the fluid therefrom, passes the partially processed smoke into the filter body 706 for further processing.

Regardless of the source, once smoke enters the filter 700, it is filtered by components housed within the filter body 706, and exits the filter 700 through the filter exhaust 710 defined by the back cap 704. As shown in FIG. 18, the filter body 706 of smoke filter 700 is cylindrical. It should be appreciated, however, that the size and/or shape of the filter body can be different. For example, the filter body can be a rectangular solid or other polygonal solid. Similarly, the front cap 702 and back cap 704 are shown as having arcuate cross-sections complementary to the shape of the filter body 706 where the front and back caps 702, 704 are coupled to the filter body 706, and the cross-sectional geometry of the front and back caps can be changed to match the shape of the filter body. In some embodiments, the filter exhaust 710 is sized and shaped to communicate with the smoke evacuation system, and the shape and/or placement of the filter exhaust 710 can remain unchanged, regardless of the size and shape the front cap 702 and/or filter body 706.

Figure 19:
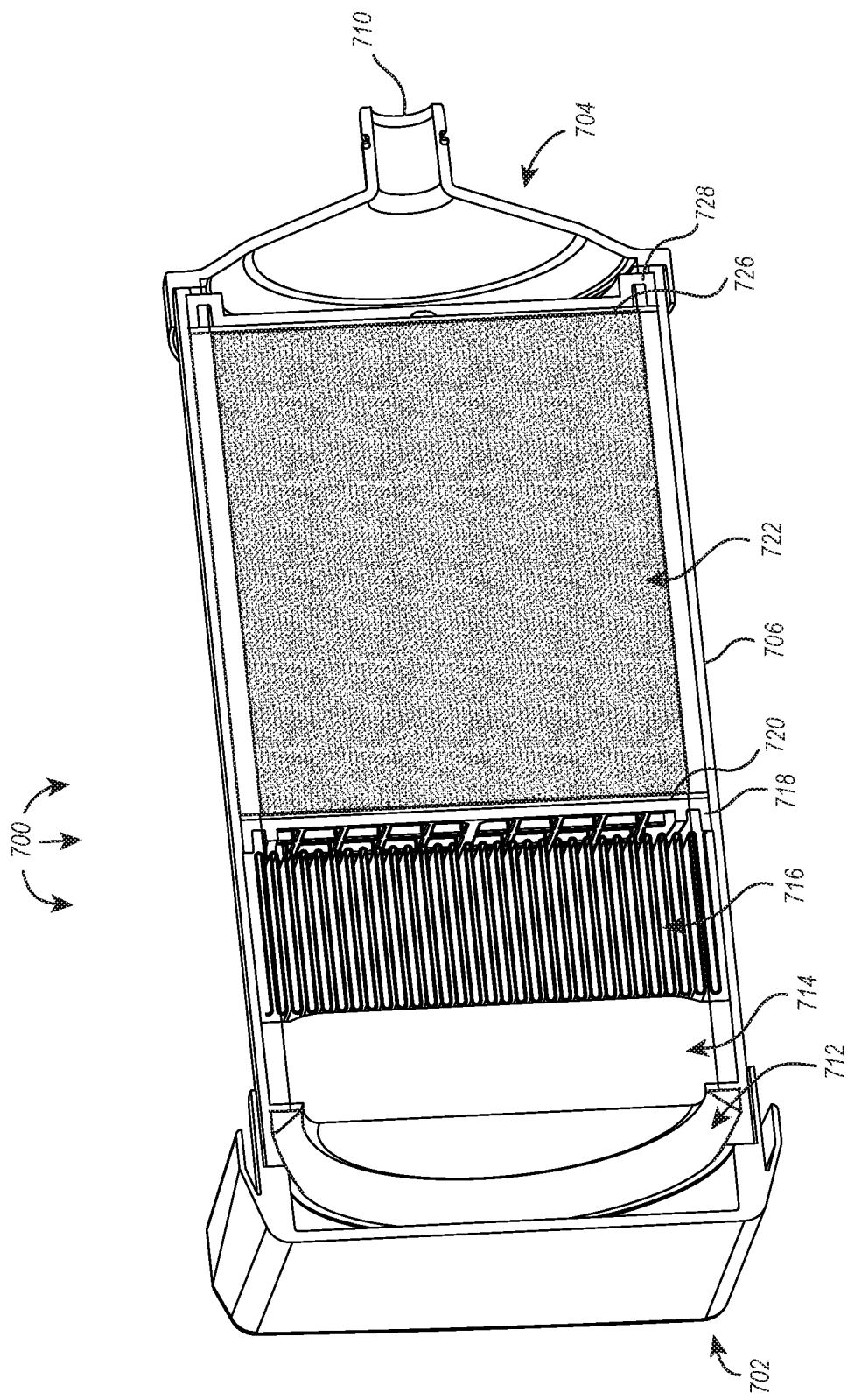
FIG. 19 illustrates a cross-section along the longitudinal axis of the exemplary smoke filter of FIG. 18, revealing various components therein.

When the filter 700 is associated with a smoke evacuation system, suction generated at the smoke evacuation system can be communicated to the filter 700 through the filter exhaust 710 to pull smoke through each of the internal filtering components of the filter 700. An exemplary embodiment of filtering components contained within smoke filter 700 is illustrated in FIG. 19. As shown, smoke entering the smoke filter 700 is initially drawn through a coarse media filter 714 followed by a fine particulate filter 716. The smoke is then drawn through a carbon reservoir 722 where gaseous contaminants such as volatile organic compounds are removed. The filtered smoke, which is now substantially free of particulate matter and gaseous contaminants, is drawn through the filter exhaust 710 and into the smoke evacuation system for further processing and/or elimination.

In some embodiments, the filter 700 can include a plurality of defined sections which can be cordoned off by one or more dams and/or dividers. As shown in FIG. 19, the smoke filter 700 can include a particulate filtration section that includes the coarse media filter 714 and the fine particular filter 716 flanked by dams 712, 718. The initial dam 712 of the particulate filtration section can be secured to an inner wall of the filter body 706 at a first end of the filter 700 proximate the front cap 702 and a first particulate filter (e.g., the coarse media filter 714) within the filter body 706. As shown in FIG. 19, the initial dam can be shaped as a gasket or O-ring and can act to prevent movement of downstream filters towards the first end or front cap 702 of the filter 700. The particulate filtration section of the filter 700 can be defined at an intermediate position within the filter body 706 by intermediate dam 718, which prevents movement of the upstream particulate filters 714, 716 toward the back cap 704. As shown in FIG. 19, the intermediate dam 718 can be shaped as a perforated disc that allows filtered smoke to freely pass through the perforations while the non-perforated sections act as a physical barrier to prevent upstream filters from moving further downstream and/or distending in the direction of applied suction.

In some embodiments, the initial dam 712 and the intermediate dam 718 are spaced apart such that the particulate filters placed therebetween are secure. In some instances, the particulate filters being secured between the initial and intermediate dams 712, 718 results in a substantial lack of lateral mobility. For example, as shown in FIG. 19, the coarse media filter 714 and fine particular filter 716 are disposed between the initial dam 712 and intermediate dam 718 such that the filters 714, 716 cannot move laterally (e.g., directionally towards or away from dams 712, 718). The size and shape of the dams, particularly intermediate dam 718 can, in some embodiments, be chosen to further prevent distention of the filters in the direction of applied suction.

The coarse media filter 714 illustrated in FIG. 19 can include any low air resistant filter, such as fiberglass, polyester, and pleated filters, that remove the majority of particulate matter larger than 10 µm. In some embodiments, this includes filters that remove at least 85% of particulate matter larger than 10 µm, greater than 90% of particulate matter larger than 10 µm, greater than 95% of particular matter larger than 10 µm, greater than 99% of particular matter larger than 10 µm, greater than 99.9% particulate matter larger than 10 µm, or greater than 99.99% particulate matter larger than 10 µm.

Additionally, or alternatively, the coarse media filter 714 can include any low air resistant filter that removes the majority of particulate matter greater than 1 µm. In some embodiments, this includes filters that remove at least 85% particulate matter larger than 1 µm, greater than 90% of particulate matter larger than 1 µm, greater than 95% of particular matter larger than 1 µm, greater than 99% of particular matter larger than 1 µm, greater than 99.9% particulate matter larger than 1 µm, or greater than 99.99% particulate matter larger than 1 µm.

The fine particulate filter 716 illustrated in FIG. 19 can include any filter of higher efficiency than the coarse media filter 714. This includes, for example, filters that are capable of filtering a higher percentage of the same sized particles as the coarse media filter 714 and/or capable of filtering smaller sized particles than the coarse media filter 714. In some embodiments, the fine particulate filter 716 can include a HEPA filter or an ULPA filter. Additionally, or alternatively, the fine particulate filter 716 can be pleated (as shown in FIG. 19) to increase the surface area of the fine particulate filter. In some embodiments, the coarse media filter 714 include a pleated HEPA filter and the fine particulate filter 716 includes a pleated ULPA filter.

Subsequent to particulate filtration, smoke enters a downstream section of the filter 700 that includes a carbon reservoir 722. In some embodiments, the carbon reservoir 722 is flanked by the intermediate dam 718 and a terminal dam 728. The terminal dam 728 can, in some embodiments, have the same shape and/or properties described above with respect to the intermediate dam 718. The carbon reservoir 722 can additionally be bounded by porous dividers 720, 726 disposed between the intermediate and terminal dams 718, 728. In some embodiments, the porous dividers 720, 726 are rigid and/or inflexible and define a constant spatial volume for the carbon reservoir 722.

In some embodiments, the carbon reservoir includes additional sorbents that act cumulatively with or independently from the carbon particles to remove gaseous pollutants. The additional sorbents can include, for example, sorbents such as magnesium oxide and/or copper oxide, which can act to adsorb gaseous pollutants such as carbon monoxide, ethylene oxide, and/or ozone. In some embodiments, the additional sorbents are dispersed throughout the reservoir or are positioned in distinct layers above, below, or within the reservoir.

Referring now to FIGS. 20-25, illustrated are simplified cross-sectional illustrations of smoke filters which can be in many respects similar to the smoke filter 700 described above. Many of the internal components of the smoke filters illustrated in FIGS. 20-25, however, have been removed for ease of illustration and discussion. It should be appreciated that the smoke filters shown in FIGS. 20-25 can include any number or combination of filter components illustrated in FIG. 19 or otherwise known in the art.

Figure 20:
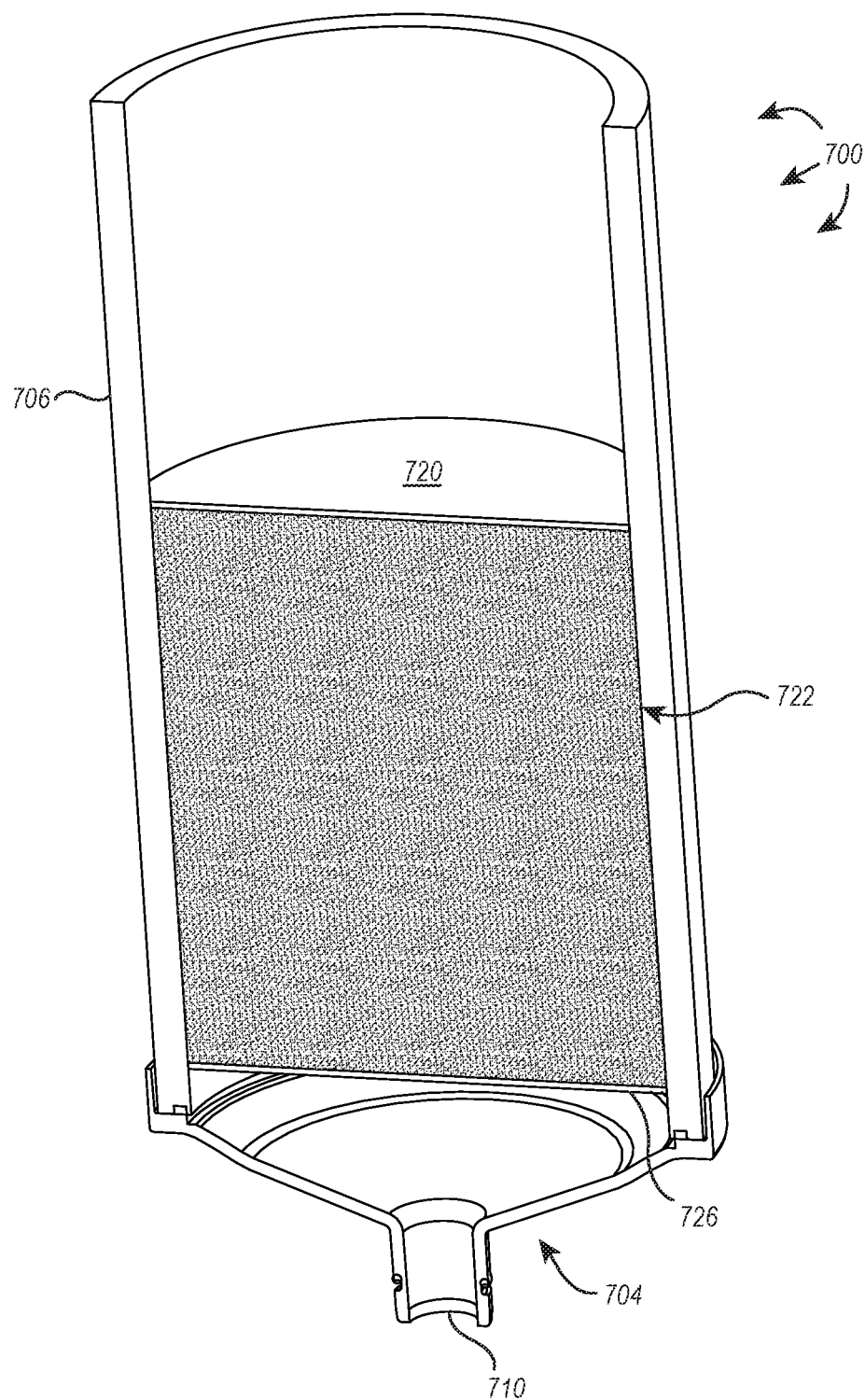
FIG. 20 illustrates a simplified view of the cross-section illustrated in FIG. 19 that emphasizes the carbon reservoir.

FIG. 20, for example, illustrates the smoke filter 700 with the carbon reservoir 722 bounded on opposite ends by porous dividers 720, 726. In some embodiments, the carbon reservoir 722 is compressed within the volume defined by the porous dividers 720, 726 when manufactured. Problematically however, the carbon reservoir 722 can settle to a smaller spatial volume over time, or when suction is applied through the carbon reservoir 722 from the filter exhaust 710, the carbon reservoir may be compacted to a smaller spatial volume. The settling or compacting of the carbon reservoir into a smaller spatial volume can create a gap within the reservoir that was previously occupied by carbon particles. In some embodiments, this can result in a nonuniform distribution of carbon particles within the reservoir, which can reduce the efficiency of adsorption and thereby reduce the effectiveness of the filter. In extreme instances, the carbon particles can settle to create a route through the reservoir that is devoid of carbon particles, allowing smoke to transit a portion or the entire length of the carbon reservoir without being adequately filtered.

Figure 21:
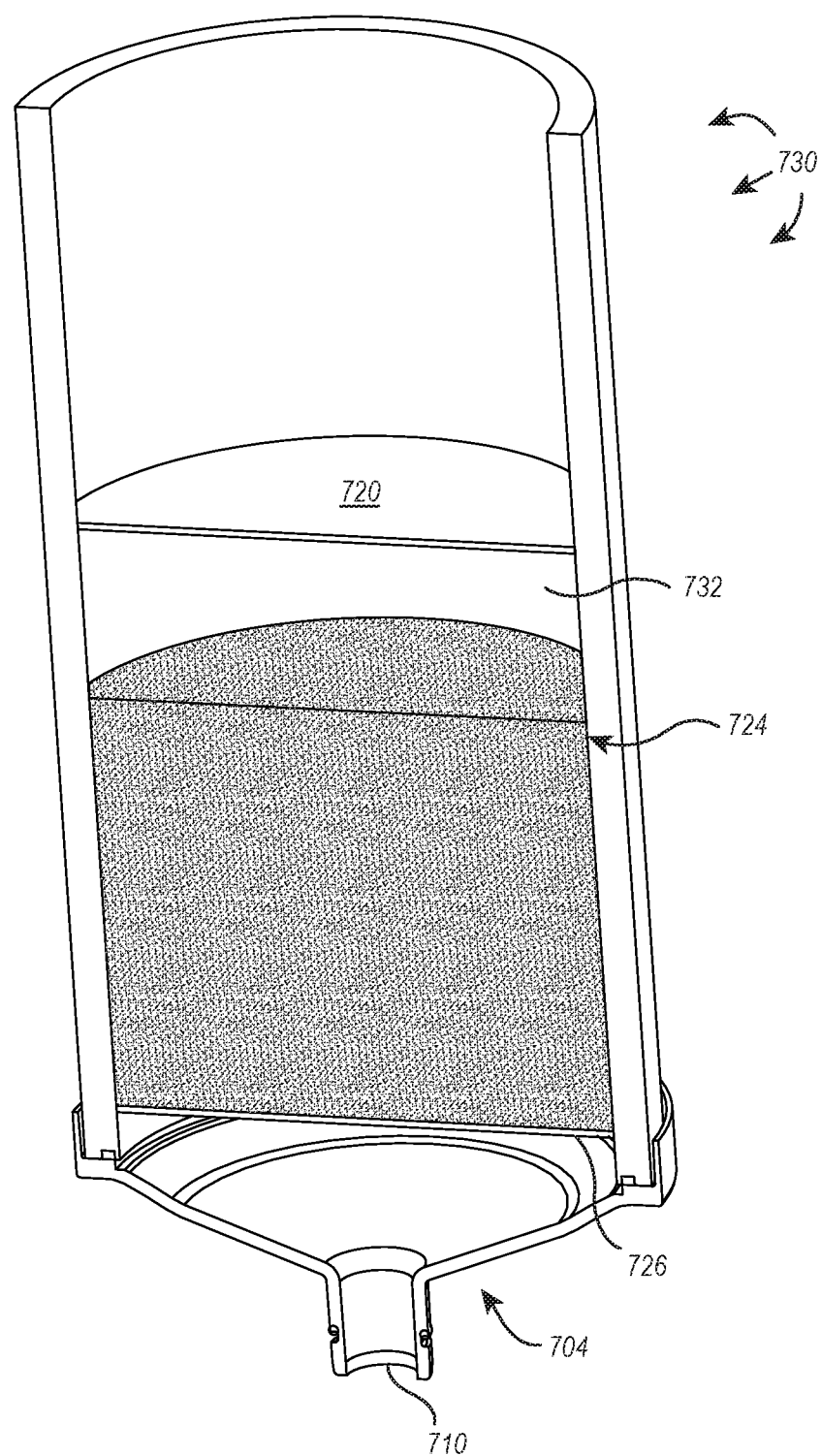
FIG. 21 illustrates the simplified view of FIG. 20 with a volumetric decrease in the carbon reservoir.

FIG. 21 illustrates a smoke filter 730 having a compacted carbon reservoir 724 that has settled over time or in response to pressure from suction communicated to the filter from a smoke evacuation system. As shown, a gap 732 is present between the compacted carbon reservoir 724 and an upstream divider 720. In some embodiments, the compacted carbon reservoir 724 filled the gap 732 before the carbon particles settled or were otherwise compacted. As shown in FIG. 21, the porous divider 720 does not move from its originally installed location as the carbon particles reorient because the porous divider 720 was fixed to the sidewalls of the smoke filter to define the carbon reservoir and/or to maintain the compressed state of the carbon reservoir.

In some embodiments, the porous divider can be replaced by a flexible porous barrier that enables the flexible porous barrier to maintain interaction with the carbon reservoir as it decreases in volume due to settling or a result of suction pressure. In doing so, the flexible porous barrier prevents gaps or channels from forming within the carbon reservoir that would otherwise decrease the efficiency or effectiveness of the carbon reservoir as a filter for gaseous contaminants.

Figure 22:
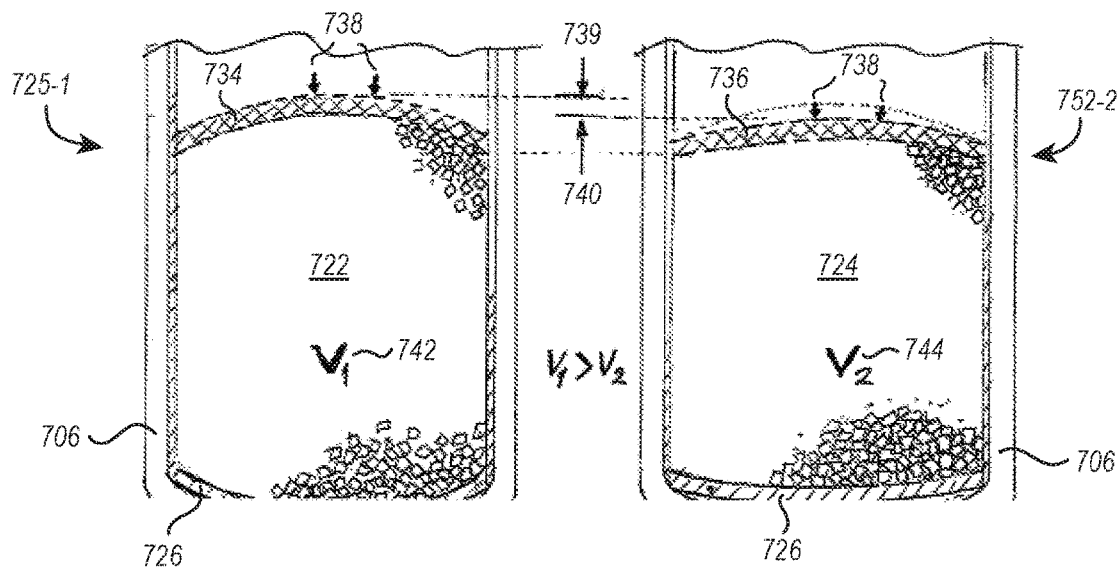
FIG. 22 illustrates cross-sections before and after a volumetric shift within a filter having a flexible porous barrier.

For example, as shown in FIG. 22, a smoke filter 725-1 includes a carbon reservoir 722 bounded on at least one end by a flexible porous barrier. The carbon reservoir 722 can be bounded on an opposing end by an inflexible porous divider 726, or in some embodiments, the carbon reservoir 722 can be bounded on an opposing end by a second flexible porous barrier (not shown). The carbon reservoir 722 is shown as occupying a first spatial volume 742—denoted $V_1$. Smoke filter 752-2 of FIG. 22 illustrates a compacted carbon reservoir 724 after settling of the carbon reservoir 722. The compacted carbon reservoir 724 now occupies a second spatial volume 744—denoted $V_2$—which is less than the first spatial volume 742. At the first spatial volume 742, the flexible porous barrier 734 is flexed and applying a compressive bias 738 against the carbon reservoir 722. As the carbon particles shift to form the compacted carbon reservoir 724, the flexed, flexible porous barrier 734 moves from a first position 739 to a second position 740 maintaining contact with the carbon particles to prevent gap formation. The partially relaxed, flexible porous barrier 736 can continue to apply a compressive bias 738 against the compacted carbon reservoir 724, and in some embodiments, the partially relaxed, flexible porous barrier 736 can move to a third position (or a plurality of subsequent positions) while continuing to apply a compressive bias against the carbon particles within the reservoir in preventing gap formation.

In some embodiments, the flexible porous barrier can flex outward, opposite the compressive bias in response to an unsettling force within the carbon reservoir. For example, the carbon particles may settle or become compacted through continuous pressure applied by suction from the smoke evacuation system. The associated flexible porous barrier may remain associated with the carbon particles as they settle, preventing gap formation (as described above). However, upon release of suction (e.g., turning the power off of the smoke evacuation system), the carbon particles may exert an outward force against the flexible porous barrier and causing it to flex toward its original position and/or return to its original position.

FIG. 22 illustrates the flexible porous barrier 734 applying a compressive bias 738 against the carbon reservoir 722 at a first side of the carbon reservoir. In some embodiments, the flexible porous barrier 734 is proximate the particulate filtration section of the smoke filter, or alternatively, the flexible porous barrier 734 is proximate the back cap. In yet other embodiments, the porous divider 726 of FIG. 22 is replaced with a second flexible porous barrier such that a flexible porous barrier defines two opposing ends of the carbon reservoir 722. It should be appreciated that regardless of the positioning or location of a flexible porous barrier with respect to the carbon reservoir, the carbon particles within the carbon reservoir may shift or settle at any position therein, and the compressive bias applied against the carbon reservoir can cause any gap or channel formed by the shifting particles to be successively filled by carbon particles disposed between the flexible porous barrier and the shifting particles.

Figure 23:
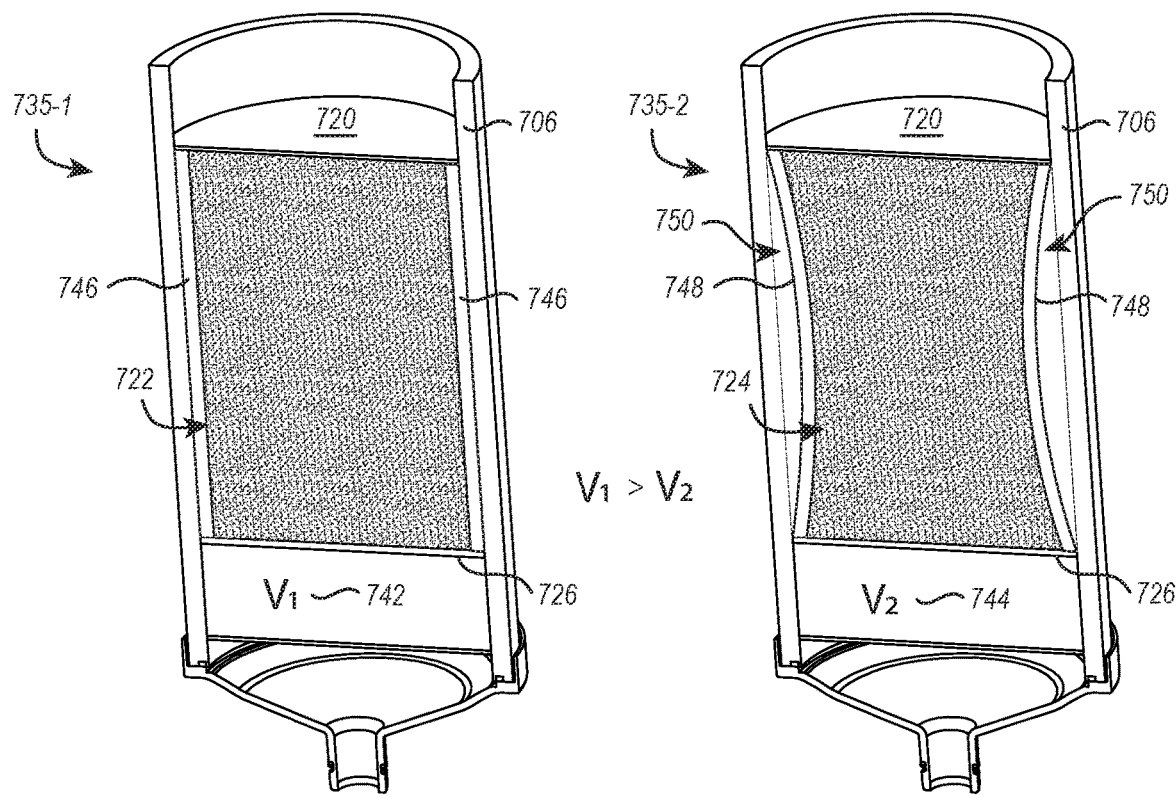
FIG. 23 illustrates cross-sections before and after a volumetric shift within another filter having a flexible porous barrier.

In some embodiments, and as illustrated in FIG. 23, a smoke filter 735-1 can include a flexible sleeve 746 that is flexed or otherwise applying an inward compressive bias against the carbon reservoir 722. Upon the carbon particles shifting from a first spatial volume 742 to a second spatial volume 744, the flexible sleeve 746 moves to a partially relaxed state, creating a gap 750 between the interior sidewall of the filter body 706 and the sleeve 748. Although FIG. 23 is illustrated as a cross-section, it should be appreciated that the sleeve 748 may, in some embodiments, wrap circumferentially around the carbon reservoir 722, 724.

Figure 24:
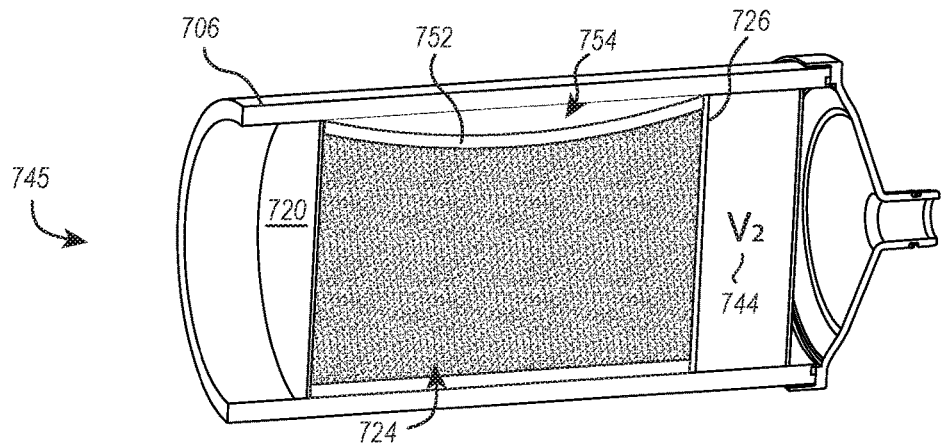
FIG. 24 illustrates a cross-section after a volumetric shift within a filter having a flexible porous barrier.

In some embodiments, and as illustrated in FIG. 24, a smoke filter 745 can include a flexible sleeve 752 that is positioned on one side and/or only partially around the carbon reservoir 724. In such an embodiment, the flexible sleeve 752 may be positioned such that when the smoke filter 745 is associated with the smoke evacuation device, the compressive bias exerted by the flexible sleeve 752 is against the carbon reservoir 724 in a direction parallel to the force of gravity. In some embodiments, the flexible sleeve 752 can be positioned about at least a portion of the carbon reservoir 724 irrespective of the directional force of gravity.

Figure 25:
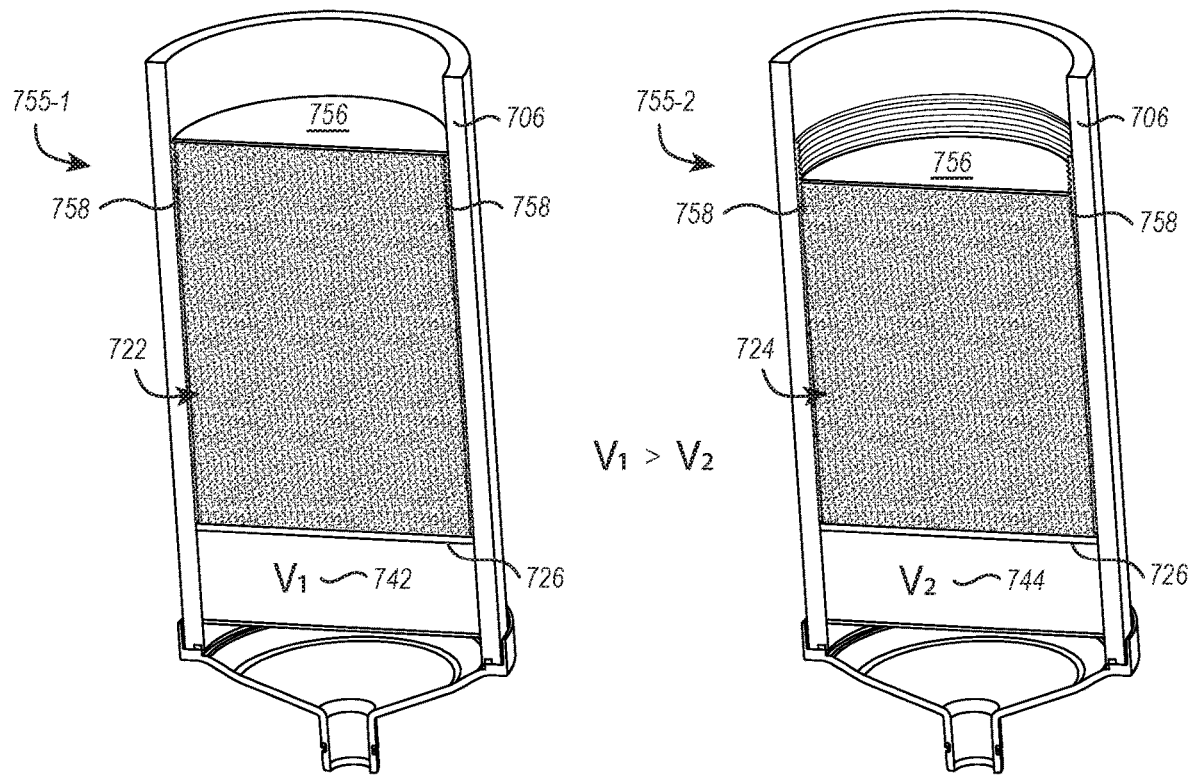
FIG. 25 illustrates cross-sections before and after a volumetric shift within a filter having a ratcheting porous barrier.

In some embodiments, a smoke filter 755-1 includes a rigid, porous barrier 756 associated with an outermost portion of the carbon reservoir 722 distal to the source of suction, as illustrated in FIG. 25. Upon shifting of carbon particles within the carbon reservoir 722 and moving from a first spatial volume 742 to a second spatial volume 744, the rigid, porous barrier ratchets down a plurality of ridges associated with the interior sidewall of the filter body 706, thereby decreasing the volume of the carbon reservoir. In some embodiments, the energy from moving the rigid, porous barrier 756 along the ridges 758 is at least partially obtained from a lack of pressure beneath the rigid, porous barrier 756—as a result of the particles shifting away from or being capable of shifting away from the barrier 756 to form a smaller, second spatial volume 744.

Additionally, or alternatively, the rigid, porous barrier 756 can be weighted more heavily such that the force of gravity causes the barrier 756 to automatically lower itself along the ridges 758 when there is sufficient space to do so. In some embodiments, the suction pressure can act to pull the barrier 756 along the ridges as there is sufficient space to do so. In some embodiments, an additional flexible member (not shown) is positioned between the barrier and another component of the filter (e.g., a dam or cap) and biases against the barrier, causing the barrier to maintain contact with the carbon particles within the reservoir as the spatial volume decreases. In some embodiments, the flexible member is a spring member that forces the barrier 756 to maintain contact with the carbon particles within the reservoir and lowers the barrier 756 along the ridges 758 when there is sufficient space to do so.

Embodiments described herein can provide a number of benefits. For example, during an electrosurgical procedure, a portion of the generated smoke can be captured and transited to a smoke evacuation system for processing and filtration. As the smoke may include particulates and gaseous pollutants, which can potentially be toxic if inhaled, decrease visibility, or at the very least be potentially odoriferous, it is advantageous to filter the smoke to a more purified state. The smoke filters described above can enable smoke to be adequately filtered.

Additionally, the smoke filters described above can prevent inefficiencies associated with gap formation when the charcoal reservoir is compacted from a starting volume to a smaller settled volume. For example, the carbon reservoir of smoke filter may compress to a smaller settled volume when under constant pressure of suction from the smoke evacuation device. This may cause gaps to form within the carbon reservoir, and smoke entering into the carbon reservoir to be filtered can pass around or through the gaps minimizing the surface area contact within the carbon reservoir. This reduced surface area contact can result in less adsorption of contaminants, and in some extreme instances, a channel may be formed partially or entirely around the carbon reservoir preventing filtration therethrough. In some embodiments, settling of the carbon particles within the reservoir may cause the carbon particles to fill a smaller spatial volume regardless of pressure. The addition of one or more flexible porous barriers and/or flexible sleeves can provide a compression bias against the particles within the carbon reservoir such that any decrease in volume causes the flexible porous barrier and/or flexible sleeve to contract inward, preventing gaps from forming.

By maintaining a solid carbon reservoir without gaps, the efficiency of the filter can be maintained or increased. Smoke being filtered through the carbon reservoir maintains contact with the surface area of carbon particles more consistently as it traverses the reservoir in beneficially increasing the efficiency of the filter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A filter, comprising:
   a filter body;
   a front cap associated with a first end of the filter body, the front cap being configured to couple to and receive smoke from a vacuum hose;
   a back cap associated with a second end of the filter body, the back cap having a filter exhaust that is sized and shaped to associate with and communicate suction from a smoke evacuation system;
   a compressed carbon reservoir disposed within the filter body between the front cap and the back cap; and
   a flexible porous barrier disposed on at least a first side of the compressed carbon reservoir, the flexible porous barrier being connected to the filter body and formed of a flexible material such that the flexible porous barrier is configured to be continuously biased towards the compressed carbon reservoir to compress the carbon reservoir.

2. The filter of claim 1, wherein the flexible porous barrier is configured to flex between at least a first position and a second position to flexibly compress the compressed carbon reservoir.

3. The filter of claim 2, wherein the flexible porous barrier transitions from a flexed state to a partially relaxed state in response to the compressed carbon reservoir reducing in volume.

4. The filter of claim 3, wherein the volume reduction of the compressed carbon reservoir is caused by one or more of a settling of the compressed carbon reservoir or a pressure from the suction communicated to the filter from the smoke evacuation system.

5. The filter of claim 2, wherein the flexible porous barrier is configured to provide the compressive bias in a same direction as the suction from the smoke evacuation system or in a direction normal to the suction from the smoke evacuation system.

6. The filter of claim 1, further comprising one or more particulate filters disposed within the filter body between the front cap and the compressed carbon reservoir.

7. The filter of claim 6, wherein the flexible porous barrier is disposed downstream of the one or more particulate filters, and wherein the first side of the compressed carbon reservoir applies a compressive bias against the compressed carbon reservoir in a direction normal to the one or more particulate filters.

8. The filter of claim 7, further comprising a dam disposed within the filter body between the one or more particulate filters and the flexible porous barrier, the dam preventing direct contact between the one or more particulate filters and the flexible porous barrier.

9. A replaceable filter for processing smoke derived from electrosurgery, the replaceable filter comprising:
   a filter body;
   a front cap associated with a first end of the filter body;
   a back cap associated with a second end of the filter body, the back cap configured to receive suction;
   one or more particulate filters disposed within the filter body between the front cap and the back cap;
   a compressed carbon reservoir disposed within the filter body between the one or more particulate filters and the back cap; and
   a flexible porous barrier connected to the filter body and disposed on at least a first side of the compressed carbon reservoir, the flexible porous barrier being disposed at least partially between the one or more particulate filters and the compressed carbon reservoir.

10. The replaceable filter of claim 9, wherein the flexible porous barrier transitions from a flexed state to a partially relaxed state in response to the compressed carbon reservoir reducing in volume.

11. The replaceable filter of claim 10, wherein the flexible porous barrier transitions from a flexed state to a partially relaxed state in a same direction as the reduction in volume of the compressed carbon reservoir.

12. The replaceable filter of claim 9, wherein the compressed carbon reservoir comprises one or more additional sorbents.

13. The replaceable filter of claim 9, wherein the one or more particulate filters comprise a coarse media filter, a high efficiency particulate air (HEPA) filter, an ultra-low penetration air (ULPA) filter, or combinations thereof.

14. The replaceable filter of claim 13, wherein the one or more particulate filters comprise a coarse media filter adjacent the front cap and a ULPA filter in series with the coarse media filter, the ULPA filter disposed between the coarse media filter and the flexible porous barrier.

15. A three-stage filter for processing smoke derived from electrosurgery, the three-stage filter comprising:
   a first stage, wherein the first stage removes one or more fluids;
   a second stage, wherein the second stage removes particulates;
   a third stage comprising a compressed carbon reservoir; and
   a flexible porous barrier disposed at least partially between the second stage and the third stage and being continuously biased towards the compressed carbon reservoir to compress the compressed carbon reservoir.

16. The three-stage filter as in claim 15, wherein the flexible porous barrier is configured to flex between at least a first position and a second position to flexibly compress the compressed carbon reservoir.

17. The three-stage filter as in claim 16, wherein the flexible porous barrier transitions from a flexed state to a partially relaxed state in response to the compressed carbon reservoir reducing in volume, the volume reduction being caused by one or more of settling of the compressed carbon reservoir or pressure from suction applied to the compressed carbon reservoir.

18. The three-stage filter as in claim 16, wherein the first stage includes a fluid trap, comprising:
   a fluid trap inlet port extending into an interior chamber of the fluid trap, the fluid trap inlet port being configured to couple to and receive smoke from a vacuum hose; and
   a fluid trap exhaust port positioned opposite and above the fluid trap inlet port, the fluid trap exhaust port defining an open channel between an interior chamber of the fluid trap, where one or more fluids extracted from the smoke are retained in the fluid trap.

19. The three-stage filter as in claim 16, wherein the second stage removes particulates using one or more particulate filters, the one or more particulate filters comprising a coarse media filter, a high efficiency particulate air (HEPA) filter, an ultra-low penetration air (ULPA) filter, or combinations thereof.

20. The three-stage filter as in claim 19, wherein the one or more particulate filters comprise the coarse media filter and the ULPA filter in series.

\* \* \* \* \*